(12) United States Patent
Hill, Jr. et al.

(10) Patent No.: US 11,935,653 B2
(45) Date of Patent: Mar. 19, 2024

(54) BLOOD TRANSFUSION MANAGEMENT USING ARTIFICIAL INTELLIGENCE ANALYTICS

(71) Applicant: University Hospitals Cleveland Medical Center, Cleveland, OH (US)

(72) Inventors: James Lee Hill, Jr., Independence, OH (US); Craig Schwabl, University Heights, OH (US); Jennifer Louise Dawson, Broadview Heights, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 475 days.

(21) Appl. No.: 17/111,708

(22) Filed: Dec. 4, 2020

(65) Prior Publication Data
US 2021/0174962 A1    Jun. 10, 2021

Related U.S. Application Data

(60) Provisional application No. 62/943,972, filed on Dec. 5, 2019.

(51) Int. Cl.
| | |
|---|---|
| *G16H 50/20* | (2018.01) |
| *G06N 5/04* | (2023.01) |
| *G06N 20/00* | (2019.01) |
| *G16H 10/60* | (2018.01) |
| *G16H 15/00* | (2018.01) |
| *G16H 20/17* | (2018.01) |

(Continued)

(52) U.S. Cl.
CPC ............. *G16H 50/20* (2018.01); *G06N 5/04* (2013.01); *G06N 20/00* (2019.01); *G16H 10/60* (2018.01);

(Continued)

(58) Field of Classification Search
CPC ........ G16H 50/20; G16H 10/60; G16H 15/00; G16H 20/17; G16H 40/20; G16H 50/70;

(Continued)

(56) References Cited

U.S. PATENT DOCUMENTS

| | | | |
|---|---|---|---|
| 10,636,521 B1 * | 4/2020 | Godfrey | ............ G06Q 30/0201 |
| 2008/0147444 A1 | 6/2008 | Jadwin et al. | |

(Continued)

FOREIGN PATENT DOCUMENTS

| | | | | |
|---|---|---|---|---|
| CN | 108511057 A | * | 9/2018 | ............ G16H 50/20 |
| WO | 2011097313 A1 | | 8/2011 | |

(Continued)

OTHER PUBLICATIONS

Foreign translation of CN-108511057-A (Year: 2018).*

(Continued)

*Primary Examiner* — Christopher L Gilligan
(74) *Attorney, Agent, or Firm* — Amin, Turocy & Watson, LLP

(57) ABSTRACT

Method and apparatus are described for a system that employs a change management algorithm to drive transfusion "appropriateness" by factoring evidenced-based knowledge and input from practitioners, where said algorithm may also ensure that a blood or blood product transfusion is provided to the right patient, that the blood/blood product is transfused at the right time, and that the procedure is completed for the right reason.

20 Claims, 17 Drawing Sheets

(51) Int. Cl.
  *G16H 40/20* (2018.01)
  *G16H 50/70* (2018.01)
  *A61M 1/02* (2006.01)

(52) U.S. Cl.
  CPC ............. *G16H 15/00* (2018.01); *G16H 20/17* (2018.01); *G16H 40/20* (2018.01); *G16H 50/70* (2018.01); *A61M 1/02* (2013.01)

(58) Field of Classification Search
  CPC ........ G16H 50/00; G16H 10/00; G16H 40/00; G06N 5/04; G06N 20/00; G06N 5/00; G06N 5/022; A61M 1/02; A61M 2205/52
  See application file for complete search history.

(56) References Cited

U.S. PATENT DOCUMENTS

| | | |
|---|---|---|
| 2012/0016686 A1 | 1/2012 | Ryan et al. |
| 2014/0278499 A1* | 9/2014 | Bowman ............ G06Q 30/0601 705/2 |
| 2016/0005139 A1 | 1/2016 | Hannon |
| 2018/0330062 A1* | 11/2018 | Balaban .................. G06N 7/01 |
| 2018/0344919 A1* | 12/2018 | Jones .................. A61M 1/1698 |

FOREIGN PATENT DOCUMENTS

| | | | | |
|---|---|---|---|---|
| WO | WO-2018086952 A1 | * | 5/2018 | |
| WO | WO-2020037244 A1 | * | 2/2020 | ............. G06N 20/00 |

OTHER PUBLICATIONS

Non-Final Office Acton for U.S. Appl. No. 17/112,218 dated Apr. 12, 2023, 35 pages.
Final Office Action for U.S. Appl. No. 17/112,218 dated Sep. 25, 2023, 24 pages.
Notice of Allowance for U.S. Appl. No. 17/112,218 dated Nov. 8, 2023, 22 pages.

* cited by examiner

FILTERS

Blood Product
☒ RBC  ☐ Platelet
☐ Plasma  ☐ Cryoprecipitate

Date Range
1/1/2015 ──○────────○── 1/1/2025

Facility
☒ Select all
☐ Facility 1
☐ Facility 2
☐ Facility 3
☐ Facility4

Department
☒ Select all
☐ Department 1
☐ Department 2
☐ Department 3
☐ Department 4

Provider
☒ Select all
☐ Provider 1
☐ Provider 2
☐ Provider 3
☐ Provider 4

[ Clear Filters ]  [ Apply Filters ]

| Facility Name | Patients | % Appropriate | Units Tranfused | Average HGB |
|---|---|---|---|---|
| Facility 1 | 44 | 52% | 72 | 6.76 |
| Facility 2 | 56 | 39% | 177 | 6.58 |
| Facility 3 | 74 | 30% | 1446 | 7.64 |
| Facility 4 | 444 | 48% | 103 | 6.55 |
| Facility 5 | 50 | 25% | 69 | 8.1 |
| Facility 6 | 29 | 47% | 15 | 6.89 |
| Facility 7 | 10 | 51% | 125 | 6.95 |
| Facility 8 | 63 | 48% | 123 | 7.22 |

| Department Name | Patients | % Appropriate | Units Tranfused | Average HGB |
|---|---|---|---|---|
| Department 1 | 22 | 39% | 72 | 6.76 |
| Department 2 | 25 | 30% | 177 | 6.58 |
| Department 3 | 33 | 48% | 1446 | 7.64 |
| Department 4 | 44 | 52% | 103 | 6.55 |
| Department 5 | 50 | 39% | 69 | 8.1 |
| Department 6 | 29 | 30% | 15 | 6.89 |
| Department 7 | 133 | 48% | 125 | 6.95 |
| Department 8 | 63 | 25% | 123 | 7.22 |
| Department 9 | 29 | 47% | 15 | 6.89 |
| Department 10 | 99 | 51% | 125 | 6.95 |
| Department 11 | 12 | 48% | 123 | 7.22 |

FIG. 7

FILTERS — 702

Blood Product
■ RBC  ☐ Platelet
☐ Plasma  ☐ Cryoprecipitate

Date Range
1/1/2015 ──○────────○── 1/1/2025

Facility
☐ Select all
■ Facility 1
☐ Facility 2
☐ Facility 3
☐ Facility4

Department
☐ Select all
■ Department 1
☐ Department 2
☐ Department 3
☐ Department 4

Provider
■ Select all
☐ Provider 1
☐ Provider 2
☐ Provider 3
☐ Provider 4

[ Clear Filters ]  [ Apply Filters ]

— 700

| Provider | Department | Visits | % Appropriate | Units Tranfused | Units Appropriate | Average HGB |
|---|---|---|---|---|---|---|
| Provider 1 | Department 1 | 5 | 69% | 72 | 55 | 6.76 |
| Provider 2 | Department 1 | 3 | 90% | 8 | 7 | 6.58 |
| Provider 3 | Department 1 | 7 | 67% | 24 | 18 | 7.64 |
| Provider 4 | Department 1 | 7 | 52% | 20 | 12 | 6.55 |
| Provider 5 | Department 1 | 5 | 70% | 37 | 30 | 8.1 |

— 704

Transfusion Procedure Details — 706

| Patient | Provider | Product Group | Appropriate | Reason | Unit Quantity |
|---|---|---|---|---|---|
| Patient 1 | Provider 1 | RBC | N | HGB out of range | 2 |
| Patient 2 | Provider 2 | RBC | Y | Hemorrage | 1 |
| Patient 3 | Provider 3 | RBC | Y | Hemorrage | 4 |
| Patient 4 | Provider 4 | RBC | Y | SvO2 < 65 | 3 |
| Patient 5 | Provider 5 | RBC | Y | Cardiac surgery | 1 |
| Patient 6 | Provider 1 | RBC | Y | HGB < 7 | 4 |
| Patient 7 | Provider 2 | RBC | Y | HGB < 7 | 2 |
| Patient 8 | Provider 3 | RBC | Y | Lactate > 2.1 | 2 |
| Patient 9 | Provider 4 | RBC | N | HGB out of range | 1 |
| Patient 10 | Provider 5 | RBC | Y | Shock | 3 |
| Patient 11 | Provider 1 | RBC | Y | Vasopressor | 3 |
| Patient 12 | Provider 2 | RBC | Y | HGB < 7 | 1 |
| Patient 13 | Provider 3 | RBC | N | HGB out of range | 2 |

FIG. 8

BLOOD TRANSFUSION MANAGEMENT USING ARTIFICIAL INTELLIGENCE ANALYTICS

RELATED APPLICATION

The subject patent application claims priority to U.S. Provisional Patent Application No. 62/943,972 filed on Dec. 5, 2019 and entitled "BLOOD TRANSFUSION MANAGEMENT USING ARTIFICIAL INTELLIGENCE ANALYTICS," the entirety of which is incorporated by reference herein.

TECHNICAL FIELD

This application relates to computer-implemented techniques for managing blood transfusions using artificial intelligence (AI) analytics.

BACKGROUND

Approximately 16 million units of blood products were transfused in the U.S in 2015. Transfusion of the appropriate blood component in the appropriate setting can be a lifesaving medical intervention, but because of inherent risks, transfusion should be administered only when clinically necessary and, ideally, evidence-based. However, transfusion practice has been shown to vary significantly between institutions and among providers within the same specialty and institution. Variability consistently points to the fact that the decision to transfuse is based on behavior, rather than scientific data, guidelines or evidence-based risk versus benefit analysis. Even though the guidelines for transfusion developed by the American Association of Blood Banks (AABB) have changed drastically in the last decade, many experienced physicians continue to practice under the old standards where physicians use their discretion when selecting viable candidates for the transfusions, the amount that should be provided to the patient, and the time that the blood transfusion should occur. Because of these lax standards, blood transfusions have been associated with higher rates of mortality and morbidity as well as increases in length of stay, readmissions, hospital-acquired infections, and other complications. Data shows that up to 60% of transfusions are either inappropriate or, at best, not demonstrably effective.

Further, current blood management systems lack the ability to account for individual patient variables to determine appropriateness of blood transfusions. When patient specific details are not accounted for, this increases the chances of the patient experiencing adverse side effects, which may include, allergic reactions, fever, anaphylaxis, and transfusion related lung injury from unnecessary transfusions. Additional transfusion risks may include blood borne infections, fluid overload, acute immune hemolytic reactions, acute renal failure, myocardial infarction, transfusion related immune modulation, increased length of stay, iron overload, graft versus host disease, to only name a few. The current systems also lack traceability as they assign blood orders to the discharging physician, and lack sufficient transparency, as they do not provide analytics/reporting at the patient and physician level.

Upon considering these issues, there remains a need to develop a system that ensures blood products are distributed to the right patients, for the right reasons, and at the right time. Further, there remains a need to track blood transfusions and generate transfusion based analytic reports about patients and the patient population.

SUMMARY

The following presents a summary to provide a basic understanding of one or more embodiments of the invention. This summary is not intended to identify key or critical elements or to delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products are described that facilitate managing blood transfusions using AI and machine learning (ML) technologies.

According to an embodiment, a system is provided that comprises at least one memory that stores computer executable components and at least one processor that executes the computer executable components stored in the memory. The computer executable components comprise a reception component that receives patient information for a patient that is a potential candidate for a transfusion procedure, wherein the patient information comprises condition information regarding a current clinical status or condition of the patient and medical history information regarding a medical history of the patient. The computer executable components can further comprise a transfusion appropriateness analysis component that employs one or more AI tactics to determine a measure of appropriateness of the transfusion procedure for the patient based on the patient information, historical transfusion data for other patients and domain knowledge transfusion data. In various embodiments, the transfusion procedure can include, but is not limited to, a blood transfusion procedure, a plasma transfusion procedure, a platelet transfusion procedure, and a cryoprecipitate transfusion procedure.

In some implementations, the measure of appropriateness comprises a transfusion appropriateness score and the computer executable components can further comprise a recommendation component that determines a recommendation regarding whether to proceed with the transfusion procedure or proceed with an alternative treatment path based on the transfusion appropriateness score. The computer executable components can further comprise a reporting component that presents recommendation data describing the recommendation to a clinician to facilitate clinical decision making for the patient prior to performance of the transfusion procedure. The computer executable components further comprise an ordering component that interfaces with one or more blood bank systems and orders a blood product for the transfusion procedure in response to a determination that the transfusion procedure is recommended.

In various implementations, the one or more AI tactics can comprise employing a transfusion appropriateness algorithm (TAA) that generates the measure of appropriateness based on a plurality of input variables included in the patient information. For example, the plurality of input variables can include clinical variables regarding the patient's current clinical state, status or condition, including but not limited to: diagnosis (e.g., any current clinical diagnosis of the patient's condition), department (e.g., perioperative, pregnancy/delivery, pediatrics/neonatal, etc.), provider specialty, reason for admittance, current course of treatment/care (e.g., including whether the patient is undergoing a clinical procedure, current phase in the perioperative process, anesthetized, etc.), current physiological parameters (e.g., vitals and laboratory measures including hemoglobin (Hgb) level, international normalized ratio (INR) level, platelet (PLT) level, fibrinogen (FIB) level, etc.), estimated blood loss, and current medications administered (e.g., TPA, anti-platelets, anti-coagulants, vasopressors, etc.). The plurality of input variables included in the patient information can also include information regarding underlying conditions/comorbidities (e.g., chronic anemia, and other relevant comorbidities), medical procedures performed and scheduled (including other transfusion procedures), allergies, medication history, and other relevant medical history parameters. The plurality of input variables included in the patient information can also include non-clinical variables, such as demographic variables pertaining to the patient (e.g., age, gender, ethnicity, height/weight, body mass index (BMI), location, etc.). In some implementations, the TAA can also factor in variables pertaining to availability of resources (e.g., blood and blood products), the current and anticipated demand, the priority level of the patient relative to other patients, and other contextual factors.

The computer executable components can further comprise an outcomes forecasting component that forecasts expected outcomes of the transfusion procedure, including potential adverse outcomes and likelihood of occurrence of the adverse outcomes. The one or more AI tactics can further comprise determining the measure of appropriateness based on the expected outcomes using a cost benefit analysis. For example, in some embodiments, input variables for the TAA can also include likelihood of one or more complications/adverse outcomes.

In one or more embodiments, the TAA comprises one or more machine learning algorithms that learn correlations between the plurality of input variables and appropriateness levels of transfusion procedures based on analysis of the historical transfusion data and the domain knowledge transfusion data. In one example, the one or more machine learning algorithms can learn the correlations based on clustering of patients into different patient groups, and wherein the levels of appropriates are tailored to the different patient groups. Additionally, or alternatively, the one or more AI tactics comprise identifying a subset of the other patients that are similar to the patient based on the patient information, and determining the measure of appropriateness based on outcomes of transfusion procedures performed for the subset of the other patients.

In some implementations, the computer executable components further comprise an amount forecasting component that forecasts, in response to a determination that the transfusion procedure is recommended, an amount of blood product for the transfusion procedure based on the patient data, the measure of appropriateness, the historical transfusion data for other patients and the domain knowledge transfusion data.

According to an embodiment, a system is provided that comprises at least one memory that stores computer executable components and at least one processor that executes the computer executable components stored in the memory. The computer executable components comprise a tracking component that tracks transfusion procedure information for patients that received transfusion procedures, the transfusion procedure information comprising appropriateness scores that represent a level of appropriateness of the transfusion procedures for the patient. The computer executable components can further a performance evaluation component that evaluates appropriateness of the transfusion procedures across different verticals based on the transfusion appropriateness scores and generates corresponding reports, and a transfusion management application that provides access to the transfusion procedure information and the reports via an interactive dashboard user interface.

In some implementations, the performance evaluation component evaluates the appropriateness of the transfusion procedures grouped by one or more of, transfusion procedure type, provider, facility, department, or patient group. The computer executable components can further comprise a waste management component that identifies inappropriate transfusion procedures included amongst the transfusion procedures based on their transfusion appropriateness scores failing to satisfy a defined appropriateness level, and wherein the performance evaluation component further generates a waste management report identifying the inappropriate transfusion procedures. In some implementations, the waste management component further identifies one or more providers, facilities, departments or patient groups associated with blood product waste based on an amount or frequency of the inappropriate transfusion procedures associated therewith.

In various implementations, the transfusion appropriateness scores were determined prior to performance of the transfusion procedures using one or more transfusion appropriateness algorithms based on current clinical statuses and conditions of the patients. For example, the one or more transfusion appropriateness algorithms can comprise one or more machine learning models trained on historical transfusion data for other patients and domain knowledge transfusion data. In some implementations of these embodiments, the transfusion procedure information can further comprise post-transfusion clinical response data for the patients, and the computer executable components further comprise a model updating component that employs one or more machine learning techniques to update the one or more transfusion appropriateness algorithms based on learned imbalances between the transfusion appropriateness scores and the post-transfusion clinical response data.

In some embodiments, elements described in connection with the disclosed systems can be embodied in different forms such as a computer-implemented method, a computer program product, or another form.

DESCRIPTION OF THE DRAWINGS

FIGS. 6-8 present example interactive transfusion management UI that can be provided by the transfusion management application in accordance with one or more embodiments of the disclosed subject matter.

DETAILED DESCRIPTION

Figure 1:
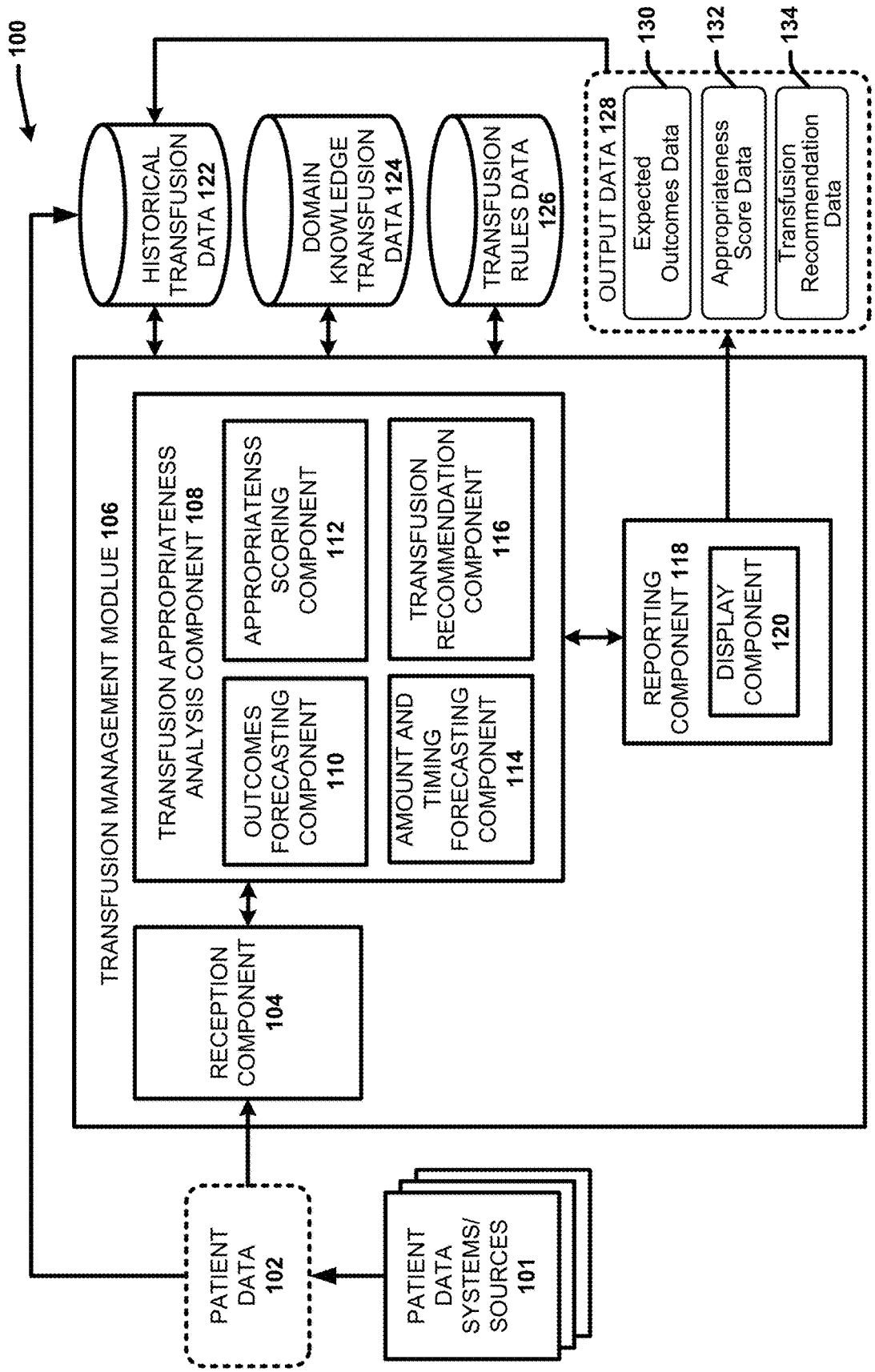
FIG. 1 illustrates a block diagram of an example, non-limiting system for managing blood transfusions using AI analytics in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Sections or in the Detailed Description section.

The disclosed subject matter is directed to systems, computer-implemented methods, apparatus and/or computer program products that provide for managing blood transfusions using artificial intelligence (AI) analytics to facilitate more effective utilization of blood products resulting in improved patient care delivery and eliminating waste of valuable donated resources. The disclosed techniques for managing blood transfusions are designed to facilitate determining what patients need transfusions, the particular type and amount of blood product needed, and the timing when needed, thereby empowering providers to take a holistic approach, using technology and people to address transfusion management.

In one or more embodiments, the disclosed transfusion management techniques employ machine learning (ML) analysis of historical blood transfusion data for different patient groups and institutions as well as clinical domain knowledge (e.g., clinical standards, textbook clinical protocols and teaching materials, expert practitioner feedback, etc.) to provide an in-depth analysis that measures and benchmarks transfusion appropriateness across a patient population. In addition, the disclosed techniques provide a full-service, real-time solution to aid healthcare organizations in extracting, organizing, reporting, and translating blood transfusion and electronic medical record (EMR) data into actionable clinical practices to improve quality of care (through standardization and per patient tailoring) and drive economic efficiency.

The disclosed transfusion management techniques were developed with some key drivers in mind. These key drivers include, but are not limited to, the need to (1) clearly define transfusion standards and appropriateness exceptions, (2) ensure that there is staff knowledge in transfusion standard expectations, (3) ensure that there is staff knowledge in massive transfusion protocol (MTP) use and ordering expectations, (4) develop a measurement system that can be filtered by provider, department, facility, system levels for blood components, etc., (5) ensure that the staff is aware of the process and outcome measurements, and (6) continual learning through plan-do-study-act (PDSAs), through scorecards, case reviews, sharing lessons learned, etc.

The present teaching is built on the premise that blood utilization decisions should be influenced by evidence-based knowledge that accounts for individual patient variables, not solely on provider preference or behavior. This is accomplished in part through the development and application of a ML model/algorithm that drives transfusion "appropriateness" by factoring evidenced-based knowledge (patient condition, risk factors, records of similar procedures, other comorbidities, etc.) and input from practitioners in over 30 different specialties and sub-specialties. This ML algorithm/model is referred to herein as the Transfusion Appropriateness Algorithm (TAA). In addition to determining the appropriateness, the evidence-based knowledge and input used by the TAA may also be critical in determining who should receive the transfusion, what amount should be transfused, when the transfusion should take place, and/or why the patients have been deemed viable candidates for the transfusion. In this regard, through use of the TAA, the disclosed techniques can reduce variability in transfusion practices by encouraging adherence to standards of care based on published guidelines and clinical patient-specific variables.

In one or more embodiments, the TAA results can be viewed in a user interface dashboard. The dashboard can inform care providers regarding relevant patient data and clinical guidelines, thereby enhancing decision making while maintaining provider autonomy. In some embodiments, the disclosed systems can send computerized alerts and reminders to clinicians as well as care providers. Where applicable, the alerts and reminders can prompt clinicians and/or providers to view clinical guidelines, condition-specific order sets, focused patient data reports and summaries, documentation templates, diagnostic support, and contextually relevant reference information, among other things. In addition, the TAA results can be used for continual learning purposes, such as, plan-do-study-act (PDSAs) cycles, scorecard measurement, case reviews, sharing lessons learned from practice evaluation, and data sharing. These TAA results reflect the current, up-to-date TAA outputs, where said TAA is also a real-time algorithm that accounts for a repository of high-quality, evidence-based, tested Clinical Decision Support (CDS) knowledge modules that may be used to support the local deployment of content, to allow for local customization, and to enable rapid upgrades of context with the development of new knowledge.

When a transfusion is deemed appropriate, the disclosed systems can report these findings to the practitioner. The report can be provided in the form of a notification, an alert, a pop-up message, or any other communication tool that may be used to notify users of relevant clinical information. In some embodiments, the report can include a number of data points, where said data points can be used to assist the provider in making appropriate clinical decisions. These data points may be related to the current recommendations per diagnosis, risk or benefits per various medical record data points, etc. In the event the TAA determines a transfusion is appropriate for a patient, in some embodiments, the system can recommend the provider proceed with the transfusion procedure. The system can also recommend one or more alternate treatment paths in instances when a transfusion is deemed inappropriate by the TAA. The one or more alternative treatment paths can take into consideration the patient's risk level and the current treatment path.

In one or more additional embodiments, the disclosed systems can mine and correlate data from multiple data sources (e.g., EMRs, blood banks, financial systems, surgical systems, etc.) to determine the risks and expected outcomes of blood product transfusions for individual patients and different patient groups. These risks and expected outcomes can be outputs (results) presented to care providers as scientific-based evidence used in determining how to proceed with transfusion cases. In some examples, the results of the TAA can be integrated with and visualized within dashboard of the provider's EMR, allowing the provider to make intelligent decisions at the point of care. Information regarding inferred risks and expected outcomes can also be incorporated into the ML process so that the TAA can be adjusted to more closely reflect the risks and expected outcomes. In some implementations, the disclosed techniques can further apply the results of the TAA to predict the patients' cost of care and potential cost savings based on the incremental direct and indirect costs of a transfusion procedure. These cost related metrics can also be viewed in the dashboard and utilized to further evaluate the cost of transfusions.

In yet another embodiment, transfusion data that is determined via application of the TAA can be used to determine staffing requirements in real-time (e.g., physicians, physician assistants (PAs), nurses (RNs), etc.). In this regard, information regarding expected future transfusion rate at a particular location and/or blood bank can be used to determine how to allocate staff in real-time. In another aspect, the disclosed techniques can evaluate current and forecasted demand for blood products to facilitate resource allocation and automated ordering of blood products where and when needed. The disclosed systems can also monitor blood product supply and demand and generate alerts regarding shortages, waste (e.g., overordering and/or underutilization of resources), and the like. For example, in one implementation, the disclosed techniques can provide for determining when the prescribed amount of blood for transfusions for a particular location (e.g., hospital, clinic, etc.), time frame, patient population, or the like, exceeds a predefined allotment. When this occurs, the ordered blood components can be reduced accordingly, resulting in a reduction in waste. In addition, guidelines can be adjusted to account for the new insights provided by the TAA based on data from many different locations, regions and patient populations. The system can also determine expected blood product utilization demands and automatically adjust blood bank inventory levels to stock necessary products for care while minimizing waste.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 for managing blood transfusions using AI analytics in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a transfusion management module 106 that can be and include computer/machine executable components. In the embodiment shown, the computer/machine executable components of the transfusion management module 106 include reception component 104, transfusion appropriateness analysis component 108 and reporting component 118. The transfusion appropriateness analysis component 108 further includes several additional machine/computer executable components, including outcomes forecasting component 110, appropriateness scoring component 112, amount and timing forecasting component 114 and transfusion recommendation component 116. These computer/machine executable components (and others described herein) can be stored in memory (not shown) associated with the one or more machines (not shown). The memory can further be operatively coupled to at least one processor (not shown), such that the components (e.g., the transfusion management module 106 itself, the reception component 104, the transfusion appropriateness analysis component 108, the reporting component 118 and other components described herein), can be executed by the at least one processor to perform the operations described. Examples of said and memory and processor as well as other suitable computer or computing-based elements, can be found with reference to FIG. 8, and can be used in connection with implementing one or more of the systems or components shown and described in connection with FIG. 1 or other figures disclosed herein.

In one or more embodiments, the transfusion management module 106 can provide real-time management decisions regarding what patients should receive a blood or blood product transfusion procedure. For example, the type of transfusion procedures evaluated by system 100 can include (but are not limited to), blood transfusion procedures, plasma transfusion procedures, platelet transfusion procedures, and cryoprecipitate transfusion procedures. The transfusion management module 106 can also provide real-time management decisions regarding the amount of blood/blood product for the transfusion procedure and the recommended timing for performing the transfusion procedure. The transfusion management module 106 can also provide real-time management decisions regarding expected outcomes associated with performing and/or not performing a transfusion procedure for a particular patient and/or group of patients at a certain time or within an upcoming time frame. In some embodiments, the transfusion management module 106 can further facilitate optimizing the efficiency and quality of the care delivery process while minimizing costs by optimizing blood utilization/allocation based on appropriateness, current demand, and forecasted demand for blood products, staffing, and the like over an upcoming timeframe (e.g., the next hour, the next 12 hours, the next 24 hours, the next 48 hours, the next week, the next month, etc.).

To support such operations, the transfusion management module 106 can consume patient data 102 regarding one or more current patients of a medical system/facility (e.g., a hospital, a hospital group, a clinic, a surgical center, a specialty clinic, etc.), historical transfusion data 122, domain knowledge transfusion data 124, and transfusion rules data 126.

The patient data 102 can include information regarding one or more current patients of a medical system/facility that employs system 100 to manage its' blood transfusion operations. For example, the medical system/facility can include a hospital, a group of hospitals, a clinic, a surgical center, a specialty clinic, an outpatient facility, a skilled nursing facility, an assisted living facility, a nursing home, a rehabilitation center, a post-acute care facility, and the like, or a combination thereof. In some embodiments, the medical system/facility can include in an integrated medical organization that provides various services to patients in both inpatient and outpatient settings. In this regard, as used herein, a "current patient" refers to a patient that is currently being treated by the medical system/facility. For example, a current patient can include admitted patients, emergent patients, patients receiving outpatient treatment, patients receiving long term treatment, or the like.

In various embodiments, the patient data 102 include information for a patient that is a potential candidate for a transfusion procedures and include a variety of rich information about the patient that can influence, on a per patient basis with respect to their tailored needs, whether the transfusion procedure is appropriate for the patient, as well as the appropriate timing of the transfusion, type of the transfusion procedure (e.g., blood/blood product type), and amount of blood product recommended for the transfusion. The transfusion appropriateness analysis component 108 can further process the patient data using one or more ML and AI tactics to evaluate appropriateness of the transfusion procedure for the patient and provide a recommendation regarding whether to proceed with the transfusion procedure.

In various embodiments, the patient data 102 can include information regarding the current clinical state, status and/or condition of the patient and the current course of treatment of the patient. Such information can include, but is not limited to: diagnosis information (e.g., any current clinical diagnosis of the patient's condition by diagnosis code, diagnosis related group (DRG) etc.), clinical signs/symptoms, current department of treatment (e.g., perioperative, pregnancy/delivery, pediatrics/neonatal, etc.), provider specialty, reason for admittance, location of admittance, and current course of treatment/care (e.g., including whether the patient is undergoing a clinical procedure, the type of clinical procedure, the current phase of the clinical procedure, etc.). Information regarding the current clinical state, status, and/or condition of the patient can also include current physiological parameter measure for the patient, including relevant laboratory measures and vitals. In various embodiments, the laboratory measures can include, but are not limited to, information regarding the patient's red blood cell (RBC) count, hemoglobin (Hgb) level, platelet (PLT) level, plasma international normalized ratio (INR) level, fibrinogen (FIB) level, coagulation profile, hematocrit (HTC) level, lactate level, partial pressure of oxygen ($PO_2$) levels, oxygen saturation ($SO_2$), and the like. The patient data 102 can also include real-time physiological information captured for a patient regarding monitored/reported vital signs, including but not limited to: hear rate, respiratory rate, temperature, systolic blood pressure, diastolic blood pressure, and other types of biomedical/physiological status data that can be captured and/or monitored for a patient in real-time (e.g., via one or more medical monitoring devices, implantable medical devices (IMDs, and the like). In various implementations, these physiological parameters can include real-time measures tracked and received for the patient over a period of time and thus provide a measure of changes in the physiological parameters over the course of the patient's care.

In some implementations, the patient data 102 can also include estimated blood loss of the patient. The patient data 102 can also include information regarding current medications administered and/or administered over the current course of treatment of the patient (e.g., from the time of admittance or start of care). In various embodiments, these medications can include tissue plasminogen activator (TPA), anti-platelets, anti-coagulants, and vasopressors. The patient data 102 can also include information regarding the current mental state/status of the patient, current laboratory tests/results, and current imaging study data/reports.

The patient data 102 can also include relevant medical history information for a patient. For example, the relevant medical history information can include information regarding underlying conditions/comorbidities (e.g., chronic anemia, and other relevant comorbidities), past treatments, past procedures/surgeries (e.g., including past transfusion procedures and information regarding type, timing, location, and amount of the transfusions), past diagnosis, family medical history, known allergies, past laboratory tests and associated reports/results, past imaging studies and associated reports/results, blood type, implanted medical devices (IMDs) worn by the patient, and the like. In various embodiments, the medical history information can be extracted from one or more EMRs and/or electronic heath records (EHRs) for the patient.

In some implementations, for each (or in some implementations one or more) patient, the patient data 102 can also identify and/or describe the care-path workflow to be followed for a patient, a priority level of the patient, a severity level of the patient respective patients, the physician/clinician(s) assigned to the patient, and any defined scheduling information for the patient regarding scheduled times/dates of care-path workflow events (e.g., clinical and non-clinical procedures/task to be performed, timing restrictions associated with the workflow events, etc.). In some implementations, the reception component 104 can collect, extract or otherwise receive this type of patient case data from one or more case scheduling systems, clinical ordering systems, physician notes, case manager notes, and the like.

The patient data 102 can also include real-time status information regarding the progress of the patient's course of care, including what's currently happening to the patient, where the patient is located, who is currently treating/attending to the patient, and the like. For example, for active patient cases, the patient data 102 can include a variety of real-time status information, including but not limited to: information regarding their current workflow status in their course of treatment (e.g., in surgery, in recovery, etc.), workflow events currently being performed (e.g., procedures being performed, medications being administered, movement of the patient from location A to location B, etc.), timing of workflow events (e.g., timing of initiation and/or completion of the workflow events and procedures), staff currently involved in the patient's care (e.g., physicians, nurses, technicians, etc.), information regarding the patient's current clinical/physiological status and the like. The patient data 102 can also include real-time information regarding changes in a patient's status, condition, diagnosis, workflow (e.g., new procedures/tasks to be performed), adverse reactions, tracked clinical events, tracked vital signs, tracked status and location information, tracked scheduled procedures and timing, tracked timing of medications administered and dose, and the like. In this regard, in embodiments in which patient cases follow defined workflows that include defined workflow events (e.g., procedures to be performed, tasks to be completed, etc.) to be performed in a defined order, the current state data 102 can track the progression of the workflow events and identify relevant information regarding the patient and the current workflow event underway.

In addition to clinical patient information described above, the patient data 102 can also include non-clinical information for the respective patients that can be correlated to their need/appropriateness for a transfusion procedure with respect to type, quantity, type and timing. For example, the non-clinical information can include demographic information for the patient, including but not limited to, the patient's age, gender, ethnicity, height/weight, body mass index (BMI), and home location. The patient data 102 can also include patient insurance information. The patient data 102 can also include patient preference information regarding preferences associated with receiving blood transfusions and authorization to perform blood transfusions. In some embodiments, the patient data 102 can also include physician/clinician reports and notes regarding the current state of the patient, recommended procedures, clinical orders, behavioral observations, other practitioner input, and the like. The patient information can also include information that can be used to group patients by various factors, including but not limited to: provider, DRG (diagnosis-related group), specialty, location, care level, department, date/time, facility, service line, assigned physician, timing of admittance, timing of scheduled procedures, and the like. In this regard, in some embodiments, the transfusion management module 106 can manage blood transfusions for patients grouped by location, by department, by DRG, by severity, by admittance timing, by age, by severity level, by provider, by blood type, and by insurance provider.

The historical transfusion data 122 can comprise historically recorded information regarding actual transfusion procedures that were performed on patients in the past at the medical system/facility and/or at various different medical systems/facilities around the world. In this regard the historical transfusion data 122 can include historical transfusion information for a variety of different patients/patient groups (e.g., that are associated with different diagnosis, different demographics, different transfusion amounts/types and contexts, etc.) regarding the transfusions that were performed, specific attributes associated with each patient, specific attributes associated with each transfusion procedure, and associated patient responses to the transfusion procedures. For example, the historical transfusion data 122 can include the same type of patient information for each patient that received a transfusion procedure (e.g., information regarding the clinical status, state, condition of the patient at or near the time of the transfusion procedure, diagnosis, medical history, comorbidities, medications administered, demographics, blood type, etc.).

Each (or in some implementations one or more) historical transfusion procedure can also be associated with information identifying or indicating the location where the transfusion procedure was performed (e.g., the specific hospital/clinic, the specific unit or area within the hospital or clinic, etc.), the timing of the procedure, the clinicians involved in the procedure, the type of blood product used, the source of the blood product used, the amount of blood product used, procedure details, and the like.

The historical transfusion data 122 can also include post-transfusion information for each patient that identifies or indicates the patient's response to the procedure, including information identifying or indicating adverse reactions or complications associated with the procedure. For example, the post-transfusion information can include measured physiological parameters and laboratory measures for the patient after transfusion (e.g., post-transfusion Hgb level, platelet level, INR level, FIB level, HTC level, lactate level, $PO_2$ level, $SO_2$ level, etc.). The post-transfusion information can identify or indicate whether the patient experienced any adverse reactions or complications, such as but not limited to: mortality, acquired infections (e.g., blood borne infections/diseases such as human immunodeficiency virus (HIV), hepatitis B, hepatitis C, syphilis, malaria, etc.), allergic reactions, fever, anaphylaxis, transfusion related lung injury, acute immune hemolytic reactions, acute renal failure, myocardial infarction, transfusion related immune modulation, ischemia, hemorrhage, immunosuppression, alloimmunization, septicemia, air embolism, transfusion related immune modulation, hemolysis (immediate or delayed), febrile reactions, pulmonary infiltrates, post transfusion purpura, anaphylactic shock, urticaria, increased length of stay (LOS), fluid overload, iron overload, and graft versus host disease.

The historical transfusion data 122 can further include additional performance related metrics associated with past patients/transfusion procedures regarding the effectiveness and cost of the transfusion. For example, the additional performance metrics can include but are not limited to, including information identifying or indicating whether hemodynamic stability was achieved, whether quality of life was improved. The additional performance metrics can also include information regarding morbidity rate associated with the transfusion procedures, patient length of stay (LOS), patient readmission rate, cost of care, cost of care attributed to the transfusion procedure and the like. The historical transfusion data 122 can be searchable/filterable and/or indexed based on various parameters, including but not limited to: provider, location, department, number/amount of blood components, DRG (diagnosis-related group), specialty, location, care level, department, date/time, facility, service line, trends, and patient.

In various embodiments, patients represented in the patient data 102 (e.g., current patients) can also be tracked following the transfusion appropriateness analysis performed by the transfusion appropriateness analysis component 108 to generate additional historical transfusion data 122. In this regard, as discussed in greater detail below, the transfusion appropriateness analysis component 108 can evaluate information for a potential transfusion candidate and provide a recommendation regarding the appropriateness of proceeding with a transfusion procedure. This recommendation information can be presented to the patient's clinician/physician to facilitate determining whether to proceed with the transfusion procedure. The transfusion management module 106 can further track the patient following the recommendation, including tracking whether the procedure was performed, the details of the procedure if performed and the patient's response. The transfusion management module 106 can also track information regarding the patient's clinical response if the transfusion procedure was not performed and information regarding alternative courses of treatment performed. The pre-transfusion patient data 102 and post recommendation patient data 102 can further be added to the historical transfusion data 122 to facilitate continual learning and ML optimization.

The domain knowledge transfusion data 124 can include evidence-based industry knowledge regarding accepted/best blood transfusion practices, including textbook and teaching materials, expert articles and papers, industry accepted standards of care and protocols and the like. The domain knowledge transfusion data 124 can include machine readable documents and materials accessible at various databases and data sources over the Internet, including peer-reviewed papers, white papers, expert opinions, input from practitioners in over 30 specialties and sub-specialties and the like. For example, the domain knowledge transfusion data can define base practices, industry accepted protocols for determining when a patient should have a transfusion based on the patient condition and/or context of care, the type of blood product to use, and the amount of blood product to use.

The transfusion rules data 126 can include transfusion rules/protocols defined for a specific care provider. For example, the transfusion rules data 126 can include a care provider's (or another blood transfusion entity) internal rules/protocols and accepted practices/guidelines for determining when a patient should have a transfusion based on the patient condition and/or context of care, the type of blood product to use, and the amount of blood product to use. In this regard, the transfusion rules data 126 can reflect internal transfusion operation policies/rules that are to be followed by a particular healthcare provider/facility that is employing system 100 to facilitate managing its transfusion operations. These internal rules and policies can be based on specific clinical and/or financial performance goals of the healthcare facility, specific resources of the healthcare facility, and the like. In this regard, the transfusion rules data 126 can vary for different healthcare providers/institutions.

In various embodiments, the reception component 104 can regularly and/or continuously receive the various types of patient data 102 discussed above from a variety of patient data systems/sources 101 in real-time. For example, the reception component 104 can receive the patient information from one or more from EMR systems, scheduling systems, blood banks, admission systems, financial systems, insurance systems, coding systems, physician notes/reports, laboratory report systems, imaging systems, case worker reports, case status tracking systems, patient location tracking systems/devices, patient vital signs monitoring systems, medical monitoring devices associated with the patients, and the like. In some implementations, these tracking and/or monitoring systems/devices can include systems/devices configured to receive and report user input in real-time explicitly identifying and/or indicating such status information (e.g., regarding the patient's active case status, location, workflow event progress, staff involved, etc.). These tracking and/or monitoring systems/devices can also include intelligent systems/devices configured to determine and report various real-time status information without or with minimal manual input based on analysis of sensor/device captured data signals. For example, these tracking and/or monitoring systems/devices can also include systems/devices configured determine information regarding what's currently happening to the patient (e.g., workflow events), where the patient is currently located, who is currently treating/attending to the patient, and the like based on analysis of a variety of captured data, including but not limited to: image data (e.g., using object recognition and/or other image pattern recognition technologies), audio data (e.g., using speech to text and natural language processing NPL), motion sensor data (e.g., using motion pattern recognition technology), radio frequency (RF) data, temperature sensor data, light sensor data, infrared (IR) senor data, biometric sensor data, and the like.

In this regard, the reception component 104 can collect, extract or otherwise receive patient data 102 continuously and/or regularly over the course of operation of a medical system/facility as the patient data 102 is generated by and/or entered into the one or more current state data systems/sources 101. For example, in some implementations, the reception component 104 can repeatedly extract, collect or otherwise receive patient data 102 for all or specific patients and/or patient groups according to a defined schedule (e.g., every second, every few seconds, every minute, every five minutes, every ten minutes, etc.). In other implementations, the reception component 104 can receive (e.g., in a push fashion) patient data 102 reflecting any changes to the current state of a patient as they occur (e.g., in response to entry into and/or generation by the one or more current state data sources/systems).

As described herein, a real-time computer system can be defined a computer system that performs its functions and responds to external, asynchronous events within a defined, predictable (or deterministic) amount of time. A real-time computer system such as system 100 typically controls a process (e.g., a blood transfusion process, a blood transfusion distribution/allocation process, etc.), or a controlled system (e.g., a blood transfusion system) by recognizing and responding to discrete events within predictable time intervals, and by processing and storing large amounts of data acquired from the controlled system (e.g., patient data 102). Response time and data throughput requirements can depend on the specific real-time application, data acquisition and critical nature of the type of decision support provided. In the regard, the term "real-time" as used herein with reference to processing and generating information by the transfusion management module 104 refers to performance of these actions within a defined or predictable amount of time (e.g., a few seconds, less than 10 seconds, less than a minute, etc.) between reception of the patient data 102 by the reception component 104. Likewise, the term real-time as used with reference to reception of the patient 102 refers to reception of the patient data 102 by the reception component 104 from the one or more patient data systems/sources 101 within a defined or predictable amount of time (e.g., a few seconds, less than 10 seconds, less than a minute, etc.) after the corresponding information is generated by and/or received by the one or more current state data systems/sources 101.

The transfusion appropriateness analysis component 108 can evaluate the patient data 102 in view of the historical transfusion data 122, the domain knowledge transfusion data 124 and/or the transfusion rules data 126 to generate inferences regarding transfusion needs of the patient. For example, the transfusion appropriateness analysis component 108 can determine or infer whether a patient should receive a transfusion procedure, and if so, when (e.g., timing), what type of blood product, and the amount of the blood product, (e.g., measured in units, volume or another appropriate metric).

In some embodiments, the transfusion appropriate analysis component 108 can regularly and/or continuously evaluate patient data 102 as it is received/updated in real-time to generate inferences regarding transfusion needs of the patients represented in the patient data 102. In another implementation, the transfusion appropriate analysis component 108 can be configured to perform transfusion appropriate analysis for a patient in response to a user request (e.g., by a clinician, or another entity), at the time of admittance, or in response to a defined clinical event (e.g., patient clinical status changing, in response to a procedure, in response to an adverse reaction, in response to a defined change in vital signs, etc.). In this regard, the transfusion appropriateness analysis component 108 can regularly and/or continuously evaluate current patients over their course of treatment to identify those patients that are candidates for a blood transfusion.

In various embodiments, the transfusion appropriate analysis described herein can involve the development and/or application of one or more ML/AI algorithms/models and/or combinatorial optimization algorithms based on input parameters/parameter values extracted from the patient data 102, the historical transfusion data 122, the domain knowledge transfusion data 124 and/or the transfusion rules data 126. To facilitate this analysis, the transfusion appropriateness analysis component 108 can include outcomes forecasting component 110, appropriateness scoring component 112, amount and timing forecasting component 114 and transfusion recommendation component 116.

The outcomes forecasting component 110 can employ one or more AI/ML techniques to forecast potential outcomes associated with performing and/or not performing a transfusion procedure for a patient represented in the patient data 102 based on patient specific features included in the patient data 102, and relevant information included in the historical transfusion data 122, the domain knowledge data 124 and/or the transfusion rules data 126. The outcomes can include both positive and negative outcomes. Information regarding forecasted outcomes can further be presented or otherwise output by the transfusion management module 106 as expected outcomes data 130.

For example, the outcomes forecasting component 110 can forecast potential risks associated with performing and/or not performing a transfusion procedure for a particular patient at a current point in time, at a future point in time, and/or within a defined timeframe (e.g., the next hour, the next 24 hours, etc.). In some implementations, the outcomes forecasting component 110 can also forecast the probability of the potential risks/outcomes. For example, the outcomes forecasting component 110 can examine the patient specific information regarding the medical history of the patient, the current clinical state/status of the patient, the current diagnosis of the patient, the patient demographics, comorbidities, medication regimen, etc., in view of historical transfusion data 122 for similar patients in the past, domain knowledge for patients with same or similar clinical states and contexts and the like, to predict the likelihood that the patient would experience various adverse side effects (e.g., percentage likelihood of infection, percentage likelihood of an allergic reaction, percentage likelihood of fluid overload, percentage likelihood of an acute immune hemolytic reaction, etc.). The outcomes forecasting component 110 can also forecast positive outcomes and associated likelihood. For example, the outcomes forecasting component 110 can forecast the probability that a transfusion will be effective, the probability that the patient will recover within an expected time frame, and the like. In some embodiments, the outcomes forecasting component 110 can also forecast expected length of stay, readmission rate (e.g., expected likelihood of readmission), and the like, for the patient in the event of performance and non-performance of the transfusion procedure.

The outcomes forecasting component 110 can employ various machine-learning based techniques, statistical-based techniques and/or probabilistic-based techniques to generate the expected outcome data 130 for a particular patient and/or group of patients based on the multitude of input parameters included in the patient data 102, the historical transfusion data 122, the domain knowledge transfusion data 124 and/or the transfusion rules data 126. In this context, a group of patients can refer to two or more patients grouped by one or more shared criterion such as diagnosis, location, demographic factors, timing of transfusion, medical history factors, etc. The machine learning techniques can include supervised machine learning techniques, semi-supervised machine learning techniques, unsupervised machine learning techniques, or a combination thereof. For example, the outcomes forecasting component 110 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc.

In another aspect, the outcomes forecasting component 110 can perform a set of machine learning computations associated with analysis of the patient data 102, the historical transfusion data 122, the domain knowledge transfusion data 124 and/or the transfusion rules data 126. For example, the outcomes forecasting component 110 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, Gaussian mixture model machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations.

In some embodiments, the outcomes forecasting component 110 can perform learning with respect to the patient data 102, the historical transfusion data 122, the domain knowledge transfusion data 124 and/or the transfusion rules data 126 explicitly or implicitly. The outcomes forecasting component 110 can also employ an automatic classification system and/or an automatic classification process to facilitate analysis of the patient data 102, the historical transfusion data 122, the domain knowledge transfusion data 124 and/or the transfusion rules data 126. For example, the outcomes forecasting component 110 can employ a probabilistic and/or statistical-based analysis (e.g., factoring into the analysis utilities/rewards and costs) to learn and/or generate inferences regarding timing of case workflows with respect to the patient data 102, the historical transfusion data 122, the domain knowledge transfusion data 124 and/or the transfusion rules data 126. The outcomes forecasting component 110 can also employ, for example, a support vector machine (SVM) classifier to learn and/or generate such inferences).

Additionally, or alternatively, the outcomes forecasting component 110 can employ other classification techniques associated with Bayesian networks, decision trees and/or probabilistic classification models. Classifiers employed by the outcomes forecasting component 110 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, $x=(x1, x2, x3, x4, xn)$, to a confidence that the input belongs to a class— that is, $f(x)=$confidence(class).

The appropriateness scoring component 112 can further determine information regarding appropriateness of transfusing a patient based on their patient data 102 in view of their expected outcomes data 130 (e.g., including information identifying or indicating risks, likelihood of risks and likelihood of positive and negative outcomes in association with performing and not performing the transfusion procedure for the particular patient), the historical transfusion data 122, the domain knowledge transfusion data 124 and/or the transfusion rules data 126. Similar to the outcomes forecasting component 110, the appropriateness scoring component can employ various machine-learning based techniques, statistical-based techniques and/or probabilistic-based techniques to generate the appropriateness score data 132 for a particular patient and/or group of patients based on the outcomes data 130 and a multitude of input parameters included in the patient data 102, the historical transfusion data 122, the domain knowledge transfusion data 124 and/or the transfusion rules data 126. The machine learning techniques can include supervised machine learning techniques, semi-supervised machine learning techniques, unsupervised machine learning techniques, or a combination thereof. In some implementations, the appropriateness scoring component can employ one or more mechanisms to identify a subset of historical other patients that are similar to a current patient and determine the measure of appropriateness based on outcomes of transfusion procedures performed for the subset of the other patients. In various embodiments, the appropriateness scoring component 112 can apply one or more previously developed transfusion appropriateness algorithms (TAAs) that use various patient specific features/feature values included in the patient data 102, and parameters/values included in the expected outcomes data 130 as input into the TAA to determine an appropriateness score that reflects a measure of appropriateness of proceeding with a transfusion for the patient. In some embodiments, the scoring component 112 can perform the appropriateness evaluation relative to a defined timeframe (e.g., the next hour, the next 24 hours, etc.).

The appropriateness scoring component 112 can further generate appropriateness score data 132 based on application of one or more TAA to the input data for a patient (e.g., relevant patient data 102 and forecasted outcomes data determined for the patient) that identifies or indicates the results of the TAA. For example, in some embodiments, the TAA can be configured to generate a binary score reflective of either "yes" a transfusion is recommended or "no" a transfusion is not recommended. With these embodiments, the appropriateness score data 132 can simply indicate that a transfusion is or is not recommended. In other embodiments, the TAA can generate a score that represents a degree of appropriateness of performance of a transfusion procedure for a particular patient. For example, the score can be on a scale of 1 to 100 or 1-10, wherein the higher the score the higher the degree of appropriateness that a transfusion procedure should be performed. With these embodiments, the appropriateness score data 132 can indicate the specific appropriateness score. In some embodiments, the TAA can also be configured to identify one or more reasons/parameters in the patient data that contribute to a determination that a transfusion procedure is deemed inappropriate or appropriate.

The transfusion recommendation component 116 can also employ a thresholding scheme to recommend whether to proceed or not proceed with a transfusion based on the appropriateness score generated by the TAA. For example, the transfusion recommendation component 116 can be configured to recommend a patient receive a transfusion if they receive an appropriateness score of X or higher. With these embodiments, the transfusion recommendation component 116 can generate transfusion recommendation data 134 that indicates whether a transfusion is recommended or not based on whether the appropriateness score is above or below the threshold score. In some embodiments, the transfusion recommendation component 116 can further identify key factors/parameters and/or parameter values that strongly contribute to a low or high appropriateness score or a recommendation of transfusion or no transfusion for a particular patient. These key contributing factors can further be included in the transfusion recommendation data 134.

In implementations in which a transfusion is recommended (e.g., because the appropriateness score was above the threshold score), the amount and timing forecasting component 114 can further employ one or more machine learning techniques and/or heuristic algorithms to determine information regarding a recommended amount and type of blood product and a recommended timing or time frame for performance of the transfusion. For example, the amount and timing forecasting component 114 can determine the recommended amount and timing of the transfusion based on learned and/or known correlations between patient specific factors and a context of the patient (represented in the patient data 102) and appropriate transfusion amount and timing as reflected in the historical transfusion data 122, the domain knowledge data 124 and/or the transfusion rules data 126. The amount and timing forecasting component 114 can employ same or similar machine learning techniques described with reference to the outcomes forecasting component 114. Information regarding the recommended transfusion amount and/or timing can further be included in the transfusion recommendation data 134.

The reporting component 118 can further provide output data 128 including expected outcomes data 130, the appropriateness score data 132 and the transfusion recommendation data 134 as they are respectively forecasted and determined in real-time to one or more entities at the medical care facility system to facilitate managing transfusion operations of the medical care facility in real-time. For example, in the embodiment shown, the reporting component 126 can generate output data 128 that can include the expected outcomes data 130, the appropriateness score data 132 and the transfusion recommendation data 134. In various embodiments, the output data 128 can be provided to relevant entities or users (e.g., staff at the medical facility) in real-time via a graphical user interface (GUI) tile or dashboard at one or more devices associated with the relevant entities or users.

In this regard, the output data 128 can be reported using various suitable data structures (e.g., as machine readable text, as human readable text, as a graphical visualization, etc.) and/or electronic rendering applications. For example, in some embodiments, the reporting component 118 (and/or one or more components of the medical facility system management module 104) can be integrated with or be coupled to one or more applications that provide various features and/or functionalities associated with managing transfusion operations of a medical facility system. For instance, in one implementation, the application can include care delivery management application accessible via a network-based platform (e.g., a web-application, a website, a thin client application), a centralized command center, or another suitable operating environment. The display component 120 can further provide one or more tiles/dashboards reporting the output data 128 in real-time.

For example, in the embodiment shown, the reporting component 118 can include a display component 120 configured to facilitate generating a graphical visualization and/or graphical user interface (GUI) for displaying at one or more user devices (not shown) that includes the expected outcomes data 130, the appropriateness score data 132 and the transfusion recommendation data 134. The one or more user devices can include for example, display monitors and/or computing devices associated with entities involved in the care delivery process at the dynamic medical facility system and/or involved in the patients care (e.g., staff of the hospital, the patients themselves, friends/family of the patients, etc.). In this regard, the visualization can allow a care provider, a clinician/physician or the like, to view and receive updated information regarding whether and why (e.g., as reflected by the expected outcomes data 130 and/or the appropriateness score data 132) a transfusion is recommended for a patient, and if so, information regarding the amount and timing for the transfusion.

In this regard, the deployment architecture of system 100 and other systems described herein can vary. For example, various features and functionalities of system 100 (and additional systems described herein) can be deployed using a distributed computing environment, wherein the one or more devices, sources, modules and/or components of system 100 (and other systems described herein) can be provided in a distributed manner across various interconnected (via one or more networks) systems and devices (e.g., internal systems, the cloud, two or more dedicated servers, etc.). For example, system 100 can be deployed in a cloud architecture, a virtualized enterprise architecture, or an enterprise architecture wherein one the front-end components and the back-end components are distributed in a client/server relationship. With these embodiments, one or more features and functionalities of the system 100 can be deployed as a web-application, a cloud-application, a thin client application, a thick client application, a native client application, a hybrid client application, or the like, wherein one or more of the front-end components (e.g., reporting component 118) are provided at client device (not shown) and one or more of the back-end components (e.g., the reception component 104, the transfusion appropriateness analysis component 108, etc.) are provided in the cloud, on a virtualized server, a virtualized data store, a remote server, a remote data store, a local data center, etc. (not sh11.own), and accessed via a network (e.g., the Internet). In this regard, the patient data systems/sources 106, the transfusion management module 106, one or more components of the transfusion management module 106, the historical transfusion data 122, the domain knowledge transfusion data 124, and the transfusion rules data 126 can be physically separated yet communicatively coupled via one or more networks. However, it should be appreciated however that system 100 is not limited to this architectural configuration. For example, in another embodiment, the entirety of the transfusion management module 106 can be deployed on a single local device (e.g., a desktop computer) as a local web-based application.

Figure 2:
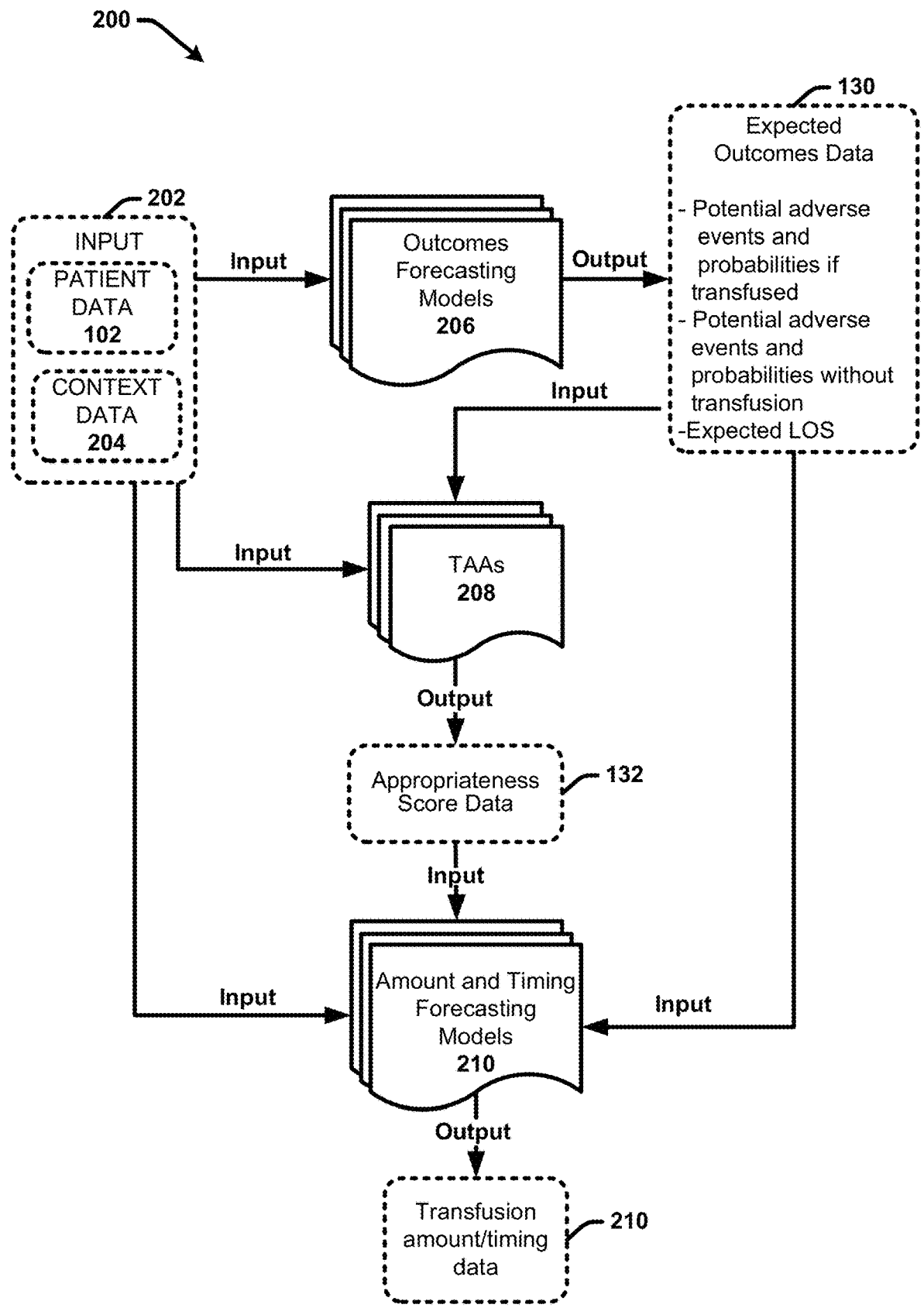
FIG. 2 presents a high-level flow diagram of an example computer implemented process for performing transfusion appropriateness analysis in accordance with one or more embodiments of the disclosed subject matter.

FIG. 2 presents a high-level flow diagram of an example computer implemented process 200 for performing transfusion appropriateness analysis in accordance with one or more embodiments of the disclosed subject matter. Repetitive description of like elements employed in respective embodiments is omitted for sake of brevity.

Process 200 involves application of one or more previously trained/developed outcomes forecasting models 206, TAAs 208 and amount and timing forecasting models 210 to input data 202 to generate outputs including expected outcomes data 130, appropriateness score data 132 and transfusion amount/timing data 210. In some embodiments, processes 200 can be tailored to a specific type of transfusion procedure. Additionally, or alternatively, process 200 can be performed for many different types of transfusion procedures, wherein the different models can be tailored to provide output data pertaining to a specific type of transfusion procedure.

In the embodiment shown, the input data 202 can include context data 204 in addition to patient data 202. The patient data 102 can include a multitude of clinical and non-clinical data points determined to be relevant in forecasting outcomes, transfusion appropriateness, and transfusion amount and timing. For example, in one or more embodiments, the clinical data points included in the patient data can include, but are not limited to limited to:

- Current clinical status/condition of the patient (e.g., anesthetized, cardiac condition, pregnancy, bleeding, organ ischemia, anemia, ischemic heart disease, underlying coronary/cardiac disease, tachycardia, hypotension, presence of active bleeding, dyspnea, etc.)
- Current diagnosis
- Underlying conditions/comorbidities (e.g., chronic anemia)
- Laboratory measures (e.g., HgB level, platelet counts, coagulation profile, INR level, FIB level, HTC level, lactate level, $PO_2$ level, $SO_2$ level, etc.)
- Vital signs and other physiological parameters (e.g., heart rate, systolic blood pressure diastolic blood pressure, respiratory rate, temperature, etc.)
- Procedures (e.g., current, past and scheduled)
- Estimated blood loss
- Other transfusions prior to or following a transfusion
- Medications (e.g., TPA, anti-platelets, anti-coagulants, and vasopressors)
- Course of care (e.g., perioperative phases, treatment phases, etc.)
- Other medical history parameters
- Reason for admittance
- Provider specialty
- Department
- Demographics (e.g., age, gender, ethnicity, height, weight, BMI, etc.)

The context data 202 can include additional contextual factors that can be factored by the one or more outcomes forecasting models 206, the one or more TAAs 208 and/or the amount and timing forecasting models 210. For example, the context data 204 can provide variables pertaining to availability of resources (e.g., blood and blood products), the current and anticipated demand for blood and blood products, the priority level of a patient relative to other patients, the location of the patient (e.g., which can significantly influence likelihood of different blood borne diseases), and other contextual factors.

With reference to FIGS. 1 and 2, in accordance with process 200, the outcomes forecasting component 110 can receive and process the patient data 102 for a potential transfusion candidate, and optionally the context data 202, using one or more outcomes forecasting models 206 to determine or infer expected outcomes data 130. The expected outcomes data 130 can include for example, potential adverse events and probabilities of occurrence of the adverse events if the transfusion procedure is performed, potential adverse events and probabilities of occurrence of the adverse events if the transfusion procedure is not performed, and expected LOS with and without the transfusion procedure. Some example adverse outcomes information that can be identified in the expected outcomes data 130 can include, but are not limited to:

Probability of mortality
Probability of different borne infections and disease (e.g., HIV, hepatitis B, hepatitis C, syphilis, malaria, etc.)
Probability of an acute immune hemolytic reactions
Probability of acute renal failure
Probability of myocardial infarction
Probability of ischemia
Probability of hemorrhage
Probability of immunosuppression
Probability of alloimmunization
Probability of Septicemia
Probability of air embolism
Probability of transfusion related immune modulation,
Probability of hemolysis (immediate or delayed)
Probability of febrile reactions
Probability of pulmonary infiltrates
Probability of post transfusion purpura
Probability of anaphylactic shock
Probability of urticaria
Probability of graft versus host disease In various embodiments, the one or more outcomes forecasting models 206, can comprise one or more previously trained/developed models/algorithms that forecast and/or facilitate forecasting the expected outcomes data 130 based on the patient data 102, the historical transfusion data 122 (e.g., which can include historical context data associated with respective historical transfusion procedures), the domain knowledge transfusion data 124, and/or the transfusion rules data 126. In this regard, previously trained/developed outcomes forecasting models can include a variety of machine learning model types, including but not limited to: a nearest neighbor model, naïve Bayes model, a decision tree model, a boosting model, a linear regression model, a neural network model, a deep neural network model, a k-means clustering model, an association rules model, q-learning model, a temporal difference algorithm, a deep adversarial network model, a classification model, or a combination thereof.

In one example, the one or more outcomes forecasting models 206 can include a classification machine learning model that maps relevant parameters included in the patient data 102 and the context data 204 to expected outcomes and/or a likelihood of occurrence of the expected outcomes. In another example, the one or more outcomes forecasting models can include one or more models trained to predict the expected outcomes information 130 based on learned correlations between different risks and outcomes and various relevant parameters (and/or the parameter values) included in the historical transfusion data 122, the domain knowledge transfusion data 124 and/or the transfusion rules data 126. With these embodiments, the outcomes forecasting component 110 can identify and extract these relevant parameters (and/or the parameter values) from the patient data 102 and the context data 204 at runtime for input to the one or more previously trained/developed outcomes forecasting models 206 to generate the expected outcomes data 130.

In some embodiments, the outcomes forecasting component 110 can employ different outcomes forecasting models 206 tailored to different transfusion procedures, different outcomes, different clinical conditions/diagnosis, and/or different patient groups. For example, the outcomes forecasting models 206 can include one or more first models tailored to forecast expected outcomes of a blood transfusion procedure, one or more second models tailored to forecast expected outcomes of a plasma transfusion procedure, one or more third models tailored to forecast expected outcomes of a platelet transfusion procedure and one or more fourth models tailored to forecast expected outcomes of a cryoprecipitate transfusion procedure. In another example, the outcomes forecasting models can include one or more first forecasting models tailored to forecast the likelihood of a first complication/risk (e.g., risk of infection), one or more second forecasting models tailored to forecast the likelihood of a second complication (e.g., risk of an acute hemolytic reaction), more third forecasting models tailored to forecast the likelihood of a third complication (e.g., risk of myocardial infarction), and so on.

In another example, the outcomes forecasting models 206 can include different outcomes forecasting models tailored to different medical conditions/diagnosis and/or patient groups grouped by one or more factors (e.g., condition/diagnosis, age, gender, location, facility, provider, department, etc.). With these embodiments, the outcomes forecasting component 110 can select and apply the applicable outcomes forecasting model based on the patient's medical condition/diagnosis and/or group to which the patient belongs as determined based on the patient data 102 for the patient.

Still on other embodiments, the outcomes forecasting component 110 can forecast the expected outcomes for a patient by identifying similar patients included in the historical transfusion data 122 and evaluating the outcomes for the similar patients. For example, in one embodiment, the one or more outcomes forecasting models can include a dimensionality reduction model (e.g., an autoencoder or another type of neural network model) configured to process the patient data 102 to generate a low-dimensional feature vector representation of key parameters in the patient data. For example, the patient data 102 can include parameters regarding the patient's current clinical status/condition, current physiological parameters/values, medical history parameters, procedure parameters, diagnosis parameters, blood loss parameters, department parameters, reason for admission parameters, and etc. With these embodiments, the dimensionality reduction model can be trained on the historical transfusion data 122 and generate reference feature vector representations for the historical transfused patients (and non-transfused patients). The outcomes forecasting models 206 can further include one or more matching networks/algorithms configured to identify a subset of similar patients to a current patient using the generated feature vector for the patient and the reference feature vectors for the historical patients. With these embodiments, the outcomes forecasting component 110 can further evaluate the outcomes data for the similar patients using one or more AI/ML statistical and/or heuristic algorithms (e.g., a weighted sum model) to determine the expected outcomes data for the current patient.

In accordance with process 200, the expected outcomes data 130 can be applied as input to the one or more TAAs 208 along with the patient data 102 and the context data 204 to generate the appropriateness score data 132. The appropriateness score data 132 can include an appropriateness sore that reflects a level of appropriateness of performing a particular transfusion procedure for the current patient. In some implementations, the appropriateness score data 132 can also identify one or more key factors impacting the appropriateness score. In various embodiments, the one or more TAAs 208 can be or include one or more previously trained/developed machine learning models/algorithms, statistical and/or heuristic models/algorithms that generate the appropriateness score data 132 based on a plurality of input variables included in the patient data 102, the context data 204 and/or the expected outcomes data 130.

In some embodiments, the one or more TAAs 208 can be trained/developed based on learned correlations between the positive and negative outcomes associated with performing and/or not performing a blood transfusion for same or similar patients in same or similar clinical contexts (as learned from the historical transfusion data 122, the domain knowledge transfusion data 124 and/or the transfusion rules data 126). For example, the one or more TAAs 208 can account for a cost/risk analysis for each patient that evaluates the costs and risks associated with performing and/or not performing a transfusion for the patient based on various patient specific parameters regarding the patient's medical history, current clinical/state, diagnosis, scheduled procedures, medication regimen, comorbidities, demographics, etc. The one or more TAAs 208 can also account for any specific transfusion rules data 126 that is applicable to the particular patient/context (e.g., regarding timing of transfusion, level of severity required before authorizing a transfusion, etc.).

In some embodiments, the appropriateness scoring component 112 can employ different TAAs 208 tailored to transfusion procedures, different clinical conditions/diagnosis, and/or different patient groups. For example, the TAAs 208 can include one or more first TAAs tailored to generate appropriateness score data 132 for a blood transfusion procedure, one or more second TAAs tailored to generate appropriateness score data 132 for a plasma transfusion procedure, one or more third TAAs tailored to generate appropriateness score data 132 for platelet transfusion procedure and one or more fourth TAAs tailored to generate appropriateness score data 132 for a cryoprecipitate transfusion procedure. In another example, the TAAs can include different TAAs tailored to different medical conditions/diagnosis and/or patient groups. For example, the one or more TAAs can include a first TAA tailored to perioperative patients, a second TAA tailored to pregnant patients, a third TAA tailored to neonatal patients, a fourth TAA tailored to patients with chronic anemia, and so on. It should be appreciated that the criteria defining a distinct patient group can vary. With these embodiments, the appropriateness scoring component 112 can select and apply the applicable TAA for a patient based on the patient's medical condition/diagnosis and/or the patient group to which the patient belongs as determined based on the patient data 102 for the patient.

In accordance with process 200 the amount and timing forecasting component 114 can further apply the appropriateness score data 132, the expected outcome data 130, the patient data 102 and/or the context data 204 can as input into one or more amount and timing forecasting models 210 to generate the transfusion amount/timing data 210. In some embodiments, this processing step can be skipped if the transfusion appropriateness score data 132 indicates that the transfusion procedure is inappropriate (e.g., if the transfusion appropriateness score is less than a threshold score).

In various embodiments, the transfusion amount and timing data 210 can identify a recommended amount of blood or blood product for the transfusion procedure. For example, the amount and timing data 210 can identify a recommended number of units of blood/blood product and/or a recommended total volume of blood/blood product determined based on various parameters included in the patient data 102, the context data 204 and/or the expected outcomes data. The transfusion amount and timing data 210 can also include information identifying or indicating timing for performance of the transfusion procedure. For example, in some implementations, the timing data can indicate a specific timeframe within which performance of the transfusion procedure is recommended (e.g., within the next ten minutes, within the next hour, within the next 2 hours, within the next 24 hours, etc.). In other implementations, the timing data can indicate number of visits over which to provide the recommended transfusion amount (e.g., two weekly visits at two units per visit).

In various embodiments, the one or more amount and timing forecasting models 210 can be or include one or more previously trained/developed machine learning models/algorithms, statistical and/or heuristic models/algorithms that generate the transfusion amount/timing data 210 based on learned correlations (e.g., as learned using the historical transfusion data 122, the domain knowledge transfusion data 124 and/or the transfusion rules data 126) between optimal transfusion amounts and transfusion timing and a plurality of input variables included in the patient data 102, the context data 204, the expected outcomes data 130 and/or the appropriateness score data 132. In some embodiments, the amount and timing forecasting models 210 can also include different models for different transfusion procedure types, different patient conditions/diagnosis, and/or different patient groups. In some embodiments, the amount and timing forecasting models 210 can factor real-time context data regarding blood product supply availability, current demand, forecasted demand, and patient priority, in association with determining the amount of blood product to provide a patient and the timing of provision.

Figure 3:
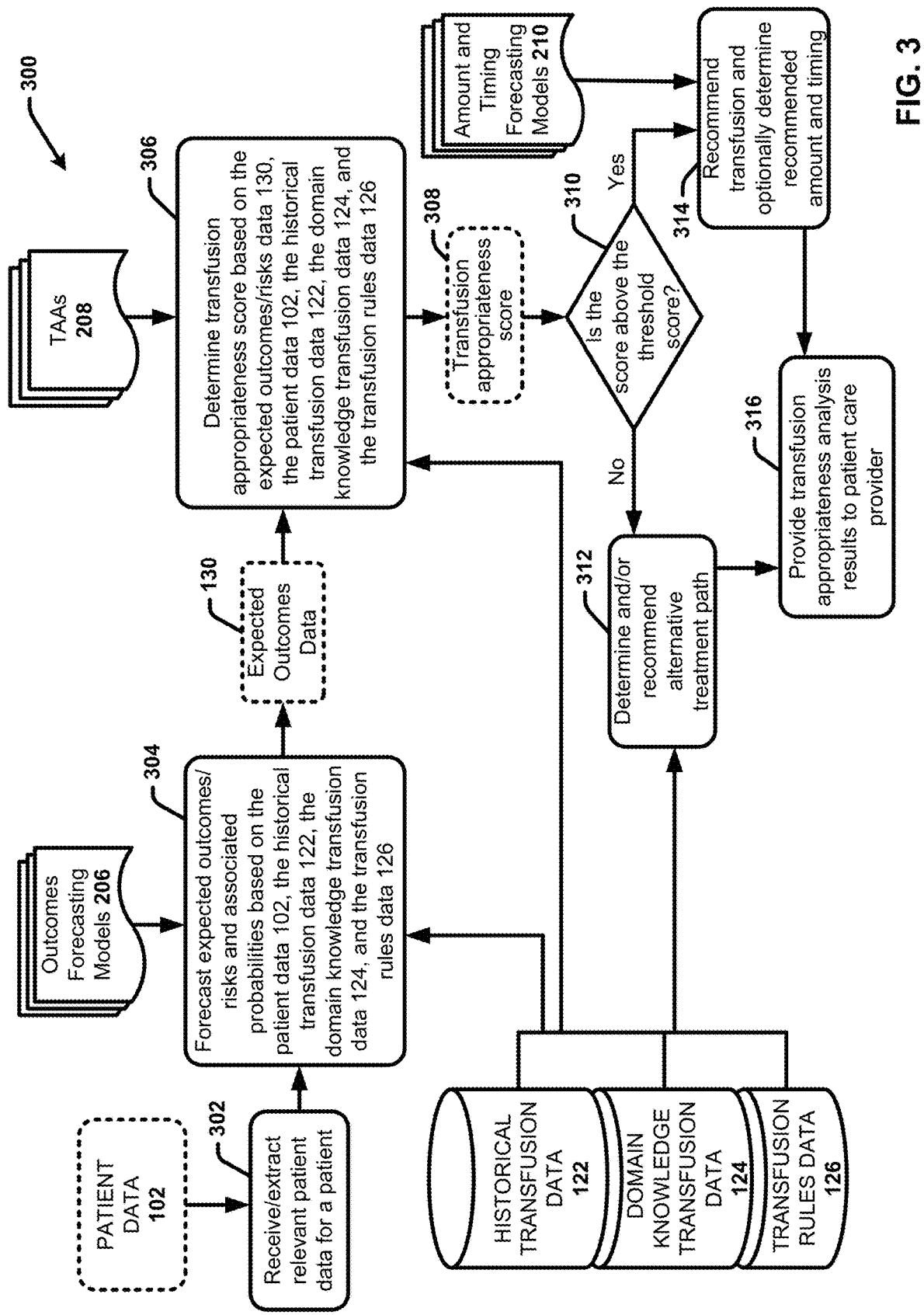
FIG. 3 presents a high-level flow diagram of an example computer implemented process for determining whether a blood transfusion is appropriate for a patient in accordance with one or more embodiments of the disclosed subject matter.

FIG. 3 presents a high-level flow diagram of an example computer implemented process 300 for determining whether a blood transfusion is appropriate for a patient in accordance with one or more embodiments of the disclosed subject matter. Repetitive description of like elements employed in respective embodiments is omitted for sake of brevity.

At 302, a system operatively coupled to a processor (e.g., system 100 and the like), can receive/extract relevant parameters included in the patient data 202 (e.g., via the reception component 104) that can be used as input to the one or more outcomes forecasting models 206, the one or more TAAs 208 and/or the amount and timing forecasting models 210. At 304, the system can forecast expected outcomes/risks and their associated probabilities of occurrence (e.g., using the outcomes forecasting component 110) based on the patient data 102, the historical transfusion data 122, and the domain knowledge transfusion data 124. In various embodiments, at 304, the outcomes forecasting can involve employing one or more outcomes forecasting models 206 to generate the expected outcomes data 130. At 306, the system can then determine a transfusion appropriateness score 308 (e.g., by the appropriateness scoring component 112) based on the expected outcomes/risks and associated probabilities, the patient data 102, the historical transfusion data 122, the domain knowledge transfusion data 124, and the transfusion rules data 126. In various embodiments, the transfusion appropriateness score 308 can be generated at 306 by the appropriateness scoring component 112 using one or more TAAs. At 310, the system can determine whether the appropriateness score is above the threshold score (e.g., using transfusion recommendation component 116). If so, then at 314, the system can recommend the transfusion procedure and optionally determine a recommended amount of blood product for the transfusion and/or a timing for performance of the transfusion (e.g., via the amount and timing forecasting component 114 using one or more amount and timing forecasting models 210). However, if at 310, the system determines that the score is not above the threshold, then at 312 the system can recommend an alternative treatment path. At 316, information regarding the transfusion appropriateness analysis results can be provided to a patient care provider (e.g., via display, a dashboard, as a notification, etc.), to facilitate clinical decision making (e.g., using the reporting component 118 and/or the display component 120).

With reference to FIGS. 1-3, as described with reference to FIG. 1 and exemplified in processes 200 and 300, the transfusion appropriate analysis component 108 can use one or more TAAs to determine the appropriateness of transfusion responses for individual patients. Evidence-based knowledge (patient's condition, risk factors, records of similar procedures, other comorbidities, etc.) and practitioner input can be extracted from blood bank and EMR databases, for example. This data can be run through the TAA and then assigned an appropriateness score, where applicable. The outcomes forecasting component 110 can also predict expected outcomes and complications related to performing and/or not performing the transfusion procedure. The results can be presented to the provider via the user interface of the dashboard, via the EMR user interface, or via another reporting mechanism.

In the event that it is determined that the transfusion is appropriate for a given patient, the reporting component 118 can indicate to the provider, through the dashboard, that it is appropriate to continue with the transfusion. In the event that it is determined that the transfusion is inappropriate for the given patient, the transfusion recommendation component 116 can recommend an alternate treatment path based on the patient's risk levels on the current treatment path. In various embodiments, the transfusion recommendation component 116 can select or determine the alternate path with the following considerations in mind: (1) the predicted outcomes and risks based on the actual or expected time period between an blood product transfusion and other clinical actions (drug administration, surgical procedure, etc.), (2) the optimal number of units or volume of blood products to be transfused based on the expected patient response or outcome (e.g. expected outcome differences between 1 and 2 units of RBC), and (3) the optimal time between prescribed recurrences of the blood product transfusions or other blood medications (e.g. a hemophiliac who requires regular transfusions on a predefined interval, or a patient that requires factor treatments on a regular basis). Although three considerations have been included herein, the areas of consideration are not limited to what has been presented above. Additional areas of consideration include, but are not limited to, comorbidities, prior and/or upcoming procedures, and various other contextual factors.

In addition to being used to determine the appropriateness of a transfusion, the evidence-based knowledge and input used in the TAA can also be critical in determining what amount should be transfused, when the transfusion should take place, and/or why the patients have been deemed viable candidates for the transfusion. The transfusion appropriateness score as well as this supporting information can be displayed to the provider/clinician via a suitable visualization/dashboard and used in the continual learning process, where continual learning strategies include, but are not limited to plan-do-study-act (PDSAs) cycles, scorecard measurement, case reviews, sharing lessons learned from practice evaluation, data sharing and model updating.

Figure 4:
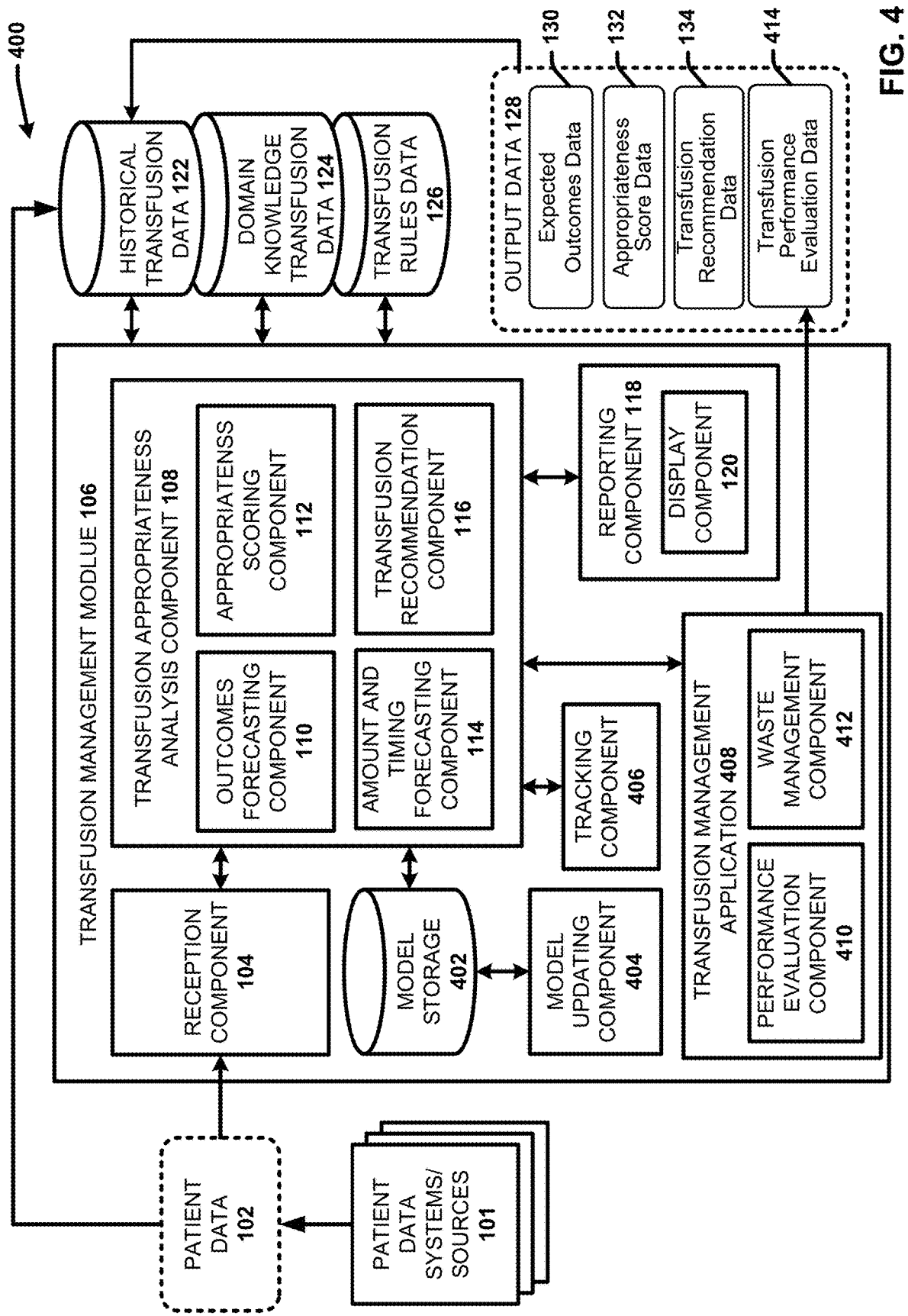
FIG. 4 illustrates a block diagram of another example, non-limiting system for managing blood transfusions using AI analytics in accordance with one or more embodiments of the disclosed subject matter.

FIG. 4 illustrates a block diagram of another example, non-limiting system 400 for managing blood transfusions using AI analytics in accordance with one or more embodiments of the disclosed subject matter. System 400 includes same or similar features and functionalities as system 100 with the addition of various components to the transfusion management module 106, including model storage 402, model updating component 404, tracking component 406, and transfusion management application 408. Repetitive description of like elements employed in respective embodiments is omitted for sake of brevity.

As noted above, in some embodiments, patient data 102 can include pre-transfusion appropriateness analysis patient data 102 and post-transfusion appropriateness analysis patient data 102 which can be tracked and added to the historical transfusion data 122 over time. To facilitate this end, the transfusion management module 106 can include tracking component 406 that track patient data 102 before and after generation of the transfusion recommendation data 134 and stores the tracked patient information in the historical transfusion data 122. The tracking component 406 can also associate the transfusion appropriateness analysis results generated for each patient with their tracked patient data in the historical transfusion data 122. In this regard, the historical transfusion data 122 can continuously grow to include information identifying many different patients across various different patient groups, the results of their transfusion appropriateness analysis (e.g., their expected outcomes data 130, the appropriateness score data 132, and their transfusion recommendation data 134), their pre-transfusion patient data 102 used to generate the transfusion appropriateness analysis results, and post-transfusion patient data that tracks the patient's clinical status/condition and treatment following the transfusion analysis. In particular, the post-transfusion analysis patient data 102 can include information identifying whether the transfusion procedure was performed or not as recommended (e.g., at the recommended amount and/or timing). If performed, the post-transfusion appropriateness analysis patient data can provide detailed tracked information regarding the patient's clinical response to the transfusion procedure and details of the transfusion procedure itself (e.g., procedure type, timing, amount of blood/blood product transfused, source of the blood/blood product, etc.). For example, the post-transfusion tracked patient data can identify changes in the patient's vitals, Hgb levels, platelet levels, etc. The post-transfusion tracked patient data can also identify any adverse reactions experienced by the patient. The post-transfusion tracked patient data can also identify the patient's LOS. The post post-transfusion analysis patient data 102 can also track patients that did not receive transfusions following the analysis, including their clinical responses (e.g., changes to their clinical status/condition) and alternative courses of treatment received.

The model updating component 404 can further perform continued learning based on the transfusion appropriates results and the tracked patient information included in the historical transfusion data 122 and update the various transfusion analysis models/algorithms accordingly. For example, in the embodiment shown, the model storage 402 can store the one or more outcomes forecasting models 206, the one or more TAAs 208, and the one or more amount and timing forecasting models 210. The model updating component 404 can further access these models in the model storage 402 can regularly update the models based on the tracked, historical transfusion data 122. In various embodiments, the model updating component can employ one or ML techniques to update models/algorithms based on learned imbalances and/or inconsistencies between the transfusion appropriateness scores and the post-transfusion recommendation treatment clinical response data (e.g., the treatment provided and the patient's clinical response/reaction to the treatment). For example, the model updating component 404 can employ one or more unsupervised and/or semi-supervised ML mechanisms to identify trends in the tracked data that indicate the outputs of one or more outcomes forecasting models 206, TAAs 208 and/or amount and timing forecasting models 210 were off.

For instance, the model updating component 404 can identify patients that received transfusion procedures as recommended that were not effective and/or were attributed to adverse outcomes, indicating retrospectively that the transfusion procedure was inappropriate. The model updating component 404 can also identify patient that did not receive transfusion procedures as recommended yet experienced unexpected adverse outcomes, indicating retrospectively that the transfusion procedure was appropriate and should have been performed. The model updating component 404 can further employ deep learning techniques to learn new correlations between various parameters and/or parameter values for the patient cases that correlate to the adverse reactions. The model updating component 404 can also identify patients whose doctors/providers went against the transfusion recommendation data 134 that received positive clinical outcomes. Based on the newly identified patterns/trends in the data, the model updating component 404 can update the models stored in the model storage 402 to provide more accurate results over time. In this regard, the model updating component 404 can learn complex correlations between a variety of different patient variables and contextual variables that influence the level of appropriateness of a transfusion procedure for a patient and update the algorithms/models accordingly so that the resulting appropriateness scores for new patients result in clinical actions and patient responses that minimize adverse outcomes and the performance of unnecessary transfusion procedures.

The transfusion management application 408 can provide an interactive management application for usage by clinicians and administrators that facilities accessing, searching, and reviewing the historical transfusion data 122 in a manner that facilitates actionable insight. To facilitate this end, the transfusion management application 408 can include performance evaluation component 410 and waste management component 412.

The performance evaluation component 410 can generate and provide interactive reports based on the historical transfusion data 122 that facilitate evaluating the performance of transfusion practices across many different organizations, departments, providers, and patient groups. The transfusion management application can further provide access to the reports via an interactive dashboard user interface (UI). In the embodiment shown, performance evaluation reports generated and provided by the transfusion management application 408 can be included in the output data 128 as transfusion performance evaluation data 414. In some embodiments, all or some of the output data 128 can be accessed and provided by the transfusion management application 408 via the interactive dashboard UI.

In various embodiments, the performance evaluation component 410 can evaluate the appropriateness of the transfusion procedures across different verticals based on the transfusion appropriateness scores and generate corresponding reports. For example, the performance evaluation component 410 can evaluate the appropriateness of the transfusion procedures grouped by one or more of, transfusion procedure type (e.g., RBC, platelet, plasma, cryoprecipitate, or another type of transfusion procedure), provider, facility, department, or patient group. The performance evaluation component 410 can further generate performance evaluation reports for each grouped vertical that summarize the level of appropriateness of the transfusions performed within each grouping. The performance evaluation component reports can identify various tracked parameters for the different transfusion procedures, including number of procedures performed, number of patients involved, amount of blood/ blood product used, and the determined appropriateness score/level of the procedures.

The transfusion management application 408 can also allow users to filter the historical transfusion data 122 and the performance evaluation reports based on provider, DRG (diagnosis-related group), specialty, location, care level, department, date/time, facility, service line, trends, and patient (chart review), to name a few filters. After filtering the data, the transfusion management application 408 can display the appropriateness metrics as they relate to the RBC (red blood cell) counts, platelet counts, plasma INR counts, Cryo FIB counts, and etc. The RBC (red blood cell) counts, platelet counts, plasma INR count, and Cryo FIB counts. For example, the transfusion performance evaluation data 414 can be displayed to the provider in the form of tables, graphs, charts, etc. Although tables, graphs, and charts have been described herein, any method for displaying the results of a data analytic process can be employed.

In some embodiments, the performance evaluation component 410 can also generate reports regarding transfusion procedures that were performed against the transfusion recommendation data 134 (e.g., performed when the appropriateness score indicated the procedure was inappropriate) and transfusion procedures that were not performed against the transfusion recommendation data 134 (e.g., not performed when the appropriateness score indicated the procedure was appropriate). These reports can also be accessed via the transfusion management application 408.

The waste management component 412 can similarly evaluate the historical transfusion data 122 to uncover waste, that is, performance of unnecessary or inappropriate transfusion procedures. In some embodiments, the waste management component 412 can identify inappropriate transfusion procedures included amongst the tracked transfusion procedures based on their transfusion appropriateness scores failing to satisfy a defined appropriateness level. The waste management component 412 or the performance evaluation component 410 can further generate a waste management report identifying the inappropriate transfusion procedures. The waste management component 412 can further identity one or more providers, facilities, departments or patient groups associated with blood product waste based on an amount or frequency of the inappropriate transfusion procedures associated therewith. For example, the waste management component 412 can identify all (or a select subset) of patient cases that were transfused against the transfusion recommendation data 134 (e.g., performed when the appropriateness score indicated the procedure was inappropriate). The waste management component 412 can further evaluate the different patient cases to identify trends and/or correlations in the cases. For example, the waste management component 412 can evaluate the cases based on the ordering provider (e.g., the doctor/clinician), the facility, the department, the patient group, and/or various other verticals to identify areas with consistent wasteful usage of blood/blood products. The waste management component 412 can further provide the waste management analysis results via the waste management application 408.

In some embodiments, the waste management component 412 can flag or otherwise track providers (e.g., ordering doctors/clinicians) that consistently transfuse patients against the transfusion recommendation data 134. Based on flagging the provider, the waste management component 412 can monitor the provider and facilitate preventing additional performance of unnecessary transfusion procedures for new patients. For example, the waste management component 412 can track the transfusion recommendation 134 generated for new patients of the provider in real-time. The waste management component 412 can further notify an administrator (or another appropriate entity) when a new patient for that provider receives a recommendation that a transfusion procedure is inappropriate. In this way, the administrator can step in and prevent the provider from performing the inappropriate procedure. Additionally, or alternatively, flagged providers (or all providers) can require additional approval before ordering transfusion procedures against the transfusion recommendation data 134. For example, the waste management component 412 can interface with a clinical ordering system, and/or an ordering system employed by the blood bank systems used to supply the transfusion procedures and flag all transfusion procedure orders (and/or blood/blood product orders) for patients whose transfusion recommendation indicated the procedure is inappropriate. The ordering system can further be configured to prevent flagged orders from proceeding without additional review and authorization (e.g., from one or more regulatory entities).

Figure 5:
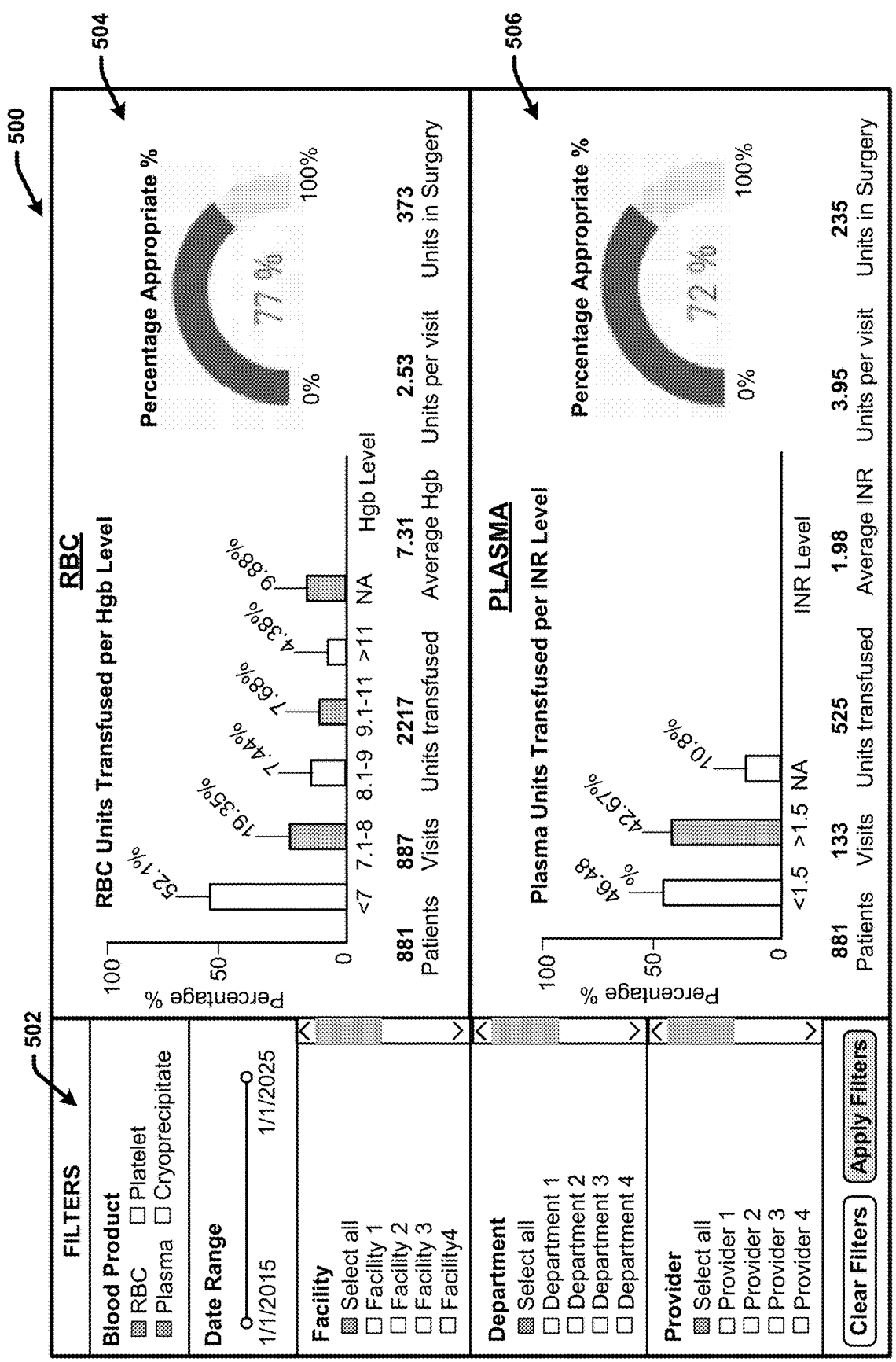
FIG. 5 presents an example transfusion management dashboard user interface (UI) in accordance with one or more embodiments of the disclosed subject matter.

FIG. 5 presents an example transfusion management dashboard UI 500 in accordance with one or more embodiments of the disclosed subject matter. The transfusion management dashboard UI 500 provides an example dashboard UI that can be generated and presented by the transfusion management application 408 based on various performance evaluation reports generated by the performance evaluation component 410.

The transfusion management dashboard UI 500 provides a summarized view of tracked transfusion procedures for different transfusion procedure types. The different transfusion procedure types in this example include RBC transfusions, plasma transfusions, platelet transfusions and cryoprecipitate transfusions. The dashboard UI 500 provides several filters 502 that can be selected to control the procedure information displayed in the primary dashboard display area. For example, the transfusion procedure data can be filtered by blood product type, date range, facility (e.g., a specific hospital/clinic location), department (e.g., cardiology, cardiovascular surgery, critical care, emergency, gastroenterology, etc.), and provider (e.g., ordering doctors/clinicians). In the embodiment shown, the RBC and plasma blood product types are selected which results in generation of an RBC summary tile 504 for the RBC transfusions and a plasma summary tile 506 for the plasma transfusions. It should be appreciated that additional tiles/windows can be generated for platelet transfusion procedures and cryoprecipitate transfusion procedures upon selection. In the embodiment shown, the transfusion procedures represented in RBC summary tile 504 and the plasma summary tile 506 cover all facilities, all departments and all providers (e.g., doctors/clinicians).

The blood product summary tiles (RBC summary tile 504 and plasma summary tile 506) respectively provide a graphical/chart summary of the percentage of transfusion procedures performed per Hgb level and INR level, respectively. For example, with reference to the RBC summary tile 504, 52.1% of the transfusion procedures were performed for patients with an Hgb level less than 7. The blood product summary tiles also summarize the total number of patients transfused, the total number of visits, the total number of units transfused, the average Hgb or INR level, the number of units per visit, and the number of units transfused during surgery. The blood product summary tiles also provide an appropriateness chart that illustrates the overall percentage of procedures determined to be appropriate (e.g., based on their transfusion appropriateness scores satisfying a defined appropriateness level). In this example, 77% of the RBC transfusion procedures were scored as appropriate and 72% of the plasma transfusion procedures were scored as appropriate.

Figure 6:
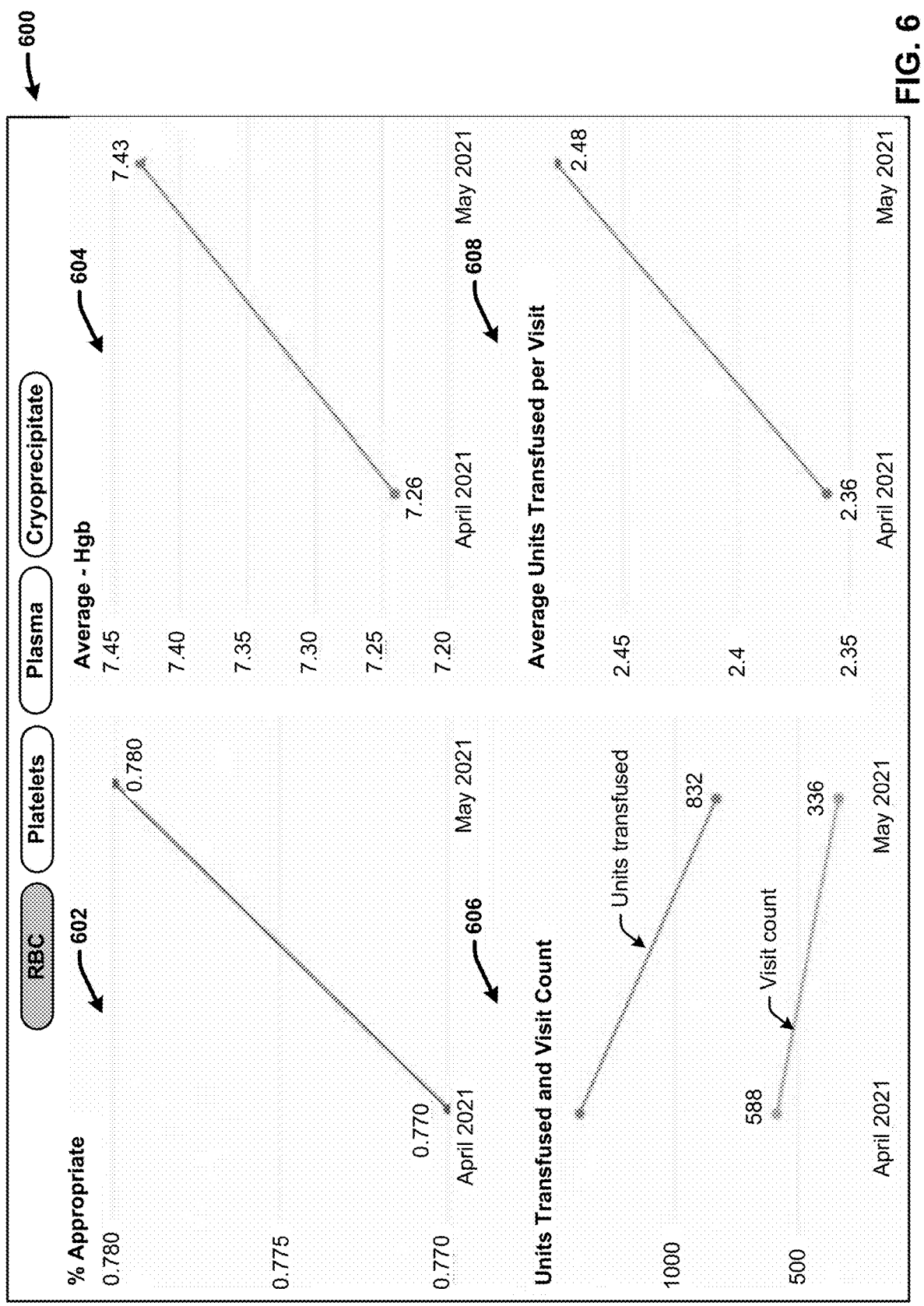

FIG. 6 presents an example interactive transfusion management UI 600 that can be provided by the transfusion management application in accordance with one or more embodiments of the disclosed subject matter. The transfusion management UI 600 provides another view of various transfusion procedure performance metrics charted as a function of time per blood product type. These charts include an appropriateness chart 602, an average Hgb chart 604, a units transfused and visit count chart 606, and an average units transfused per visit chart. In this example, the RBC blood product type is selected. In this example, the appropriateness chart 602 indicates a positive trend in the percentage of cases deemed appropriate.

FIG. 7 presents another example interactive transfusion management UI 700 that can be provided by the transfusion management application in accordance with one or more embodiments of the disclosed subject matter. Similar to the dashboard UI 500, the transfusion management UI 700 provides several filters 702 that can be selected to control the procedure information displayed in the primary dashboard display area. In this example, the primary display area includes two tables. The upper table 704 provides transfusion procedure information by facility and the lower table 706 provides transfusion procedure information by department. In this example, all departments and all facilities are selected. In various embodiments, a specific facility can be selected within the upper table 704 (and/or via the filters 702) which results in displaying a new view within the upper table 704 with transfusion details pertaining to the selected facility only. In addition, selection of a specific facility in the upper table 704 (and/or via the filters 702) can result in changing the information displayed in the lower table 706 to pertain to only that selected facility. For example, the departments in the lower table can change to include information for only those departments provided by the selected facility.

FIG. 8 presents another view of interactive transfusion management UI 700 that can be provided by the transfusion management application in accordance with one or more embodiments of the disclosed subject matter. In particular, FIG. 8 demonstrates changes to the information displayed in the upper table 704 and the lower table 706 in response to selection of one or more filters 702 from the filter menu. In this example, Facility 1 and Department 1 has been selected (along with the blood product RBC). This results in the information included in the upper table 704 including transfusion summaries for each provider within Department 1 (e.g., each ordering doctor/clinician at the selected facility. The information in the lower table 706 further changes to provide a more detailed view of the details of the different transfusion procedures performed at the selected facility within Department 1. The transfusion procedure details in the lower table 706 further provide a binary measure of whether the procedure was deemed appropriate or not (Y for yes, N for no) based on the transfusion score meeting or failing to meet a defined threshold. The transfusion procedure details also provide a primary reason for the appropriateness determination.

Figure 9:
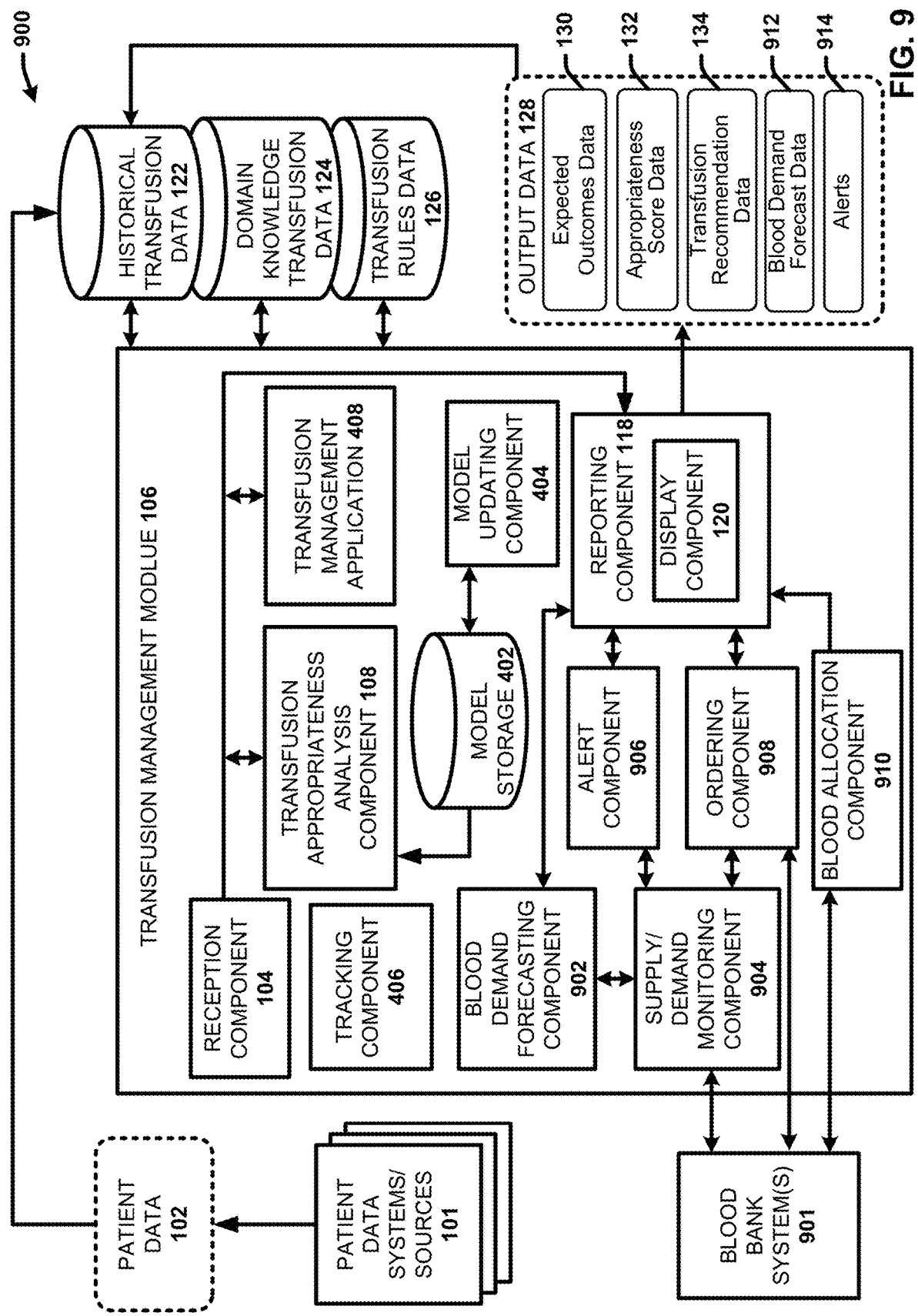
FIG. 9 illustrates a block diagram of another example, non-limiting system for managing blood transfusions using AI analytics in accordance with one or more embodiments of the disclosed subject matter.

FIG. 9 illustrates a block diagram of another example, non-limiting system 900 for managing blood transfusions using AI analytics in accordance with one or more embodiments of the disclosed subject matter. System 900 includes same or similar features and functionalities as system 100 with the addition of blood demand forecasting component 902, supply/demand monitoring component 904, alert component 906, ordering component 908 and blood allocation component 910. System 900 further includes one or more blood bank systems 401, blood demand forecast data 410 and alerts 412. Although not shown for simplification of the drawings, it should be appreciated the transfusion appropriateness analysis component 108 and the transfusion management application 408 can include their internal components discussed infra. Repetitive description of like elements employed in respective embodiments is omitted for sake of brevity.

In one or more additional embodiments, the transfusion management module 106 can include blood demand forecasting component 902 to forecast the future demand for blood products at one or more medical facilities/systems based on the current transfusion recommendations for the current patients, and the timing and amount of the current transfusion recommendation. For example, the blood demand forecasting component 902 can forecast the demand for blood products for all patients at a particular healthcare facility location/clinic within the next hour, the next 24 hours, the next 48 hours, the next week, etc., based on the current patient population and the current recommendations regarding what patients are recommended to receive transfusions, how much blood product to be received and when. In some embodiments, the blood demand forecasting component 902 can further examine the tracked historical transfusion data 122 for the medical facility (e.g., provided by the historical transfusion data) under similar contexts (e.g., patient distributions, patient occupancy levels, patient needs and diagnosis, operating conditions, etc.) to further facilitate forecasting blood demand needs for the facility over different upcoming timeframes. Information regarding forecasted blood demand needs can further be provided in the output data 128 as blood demand forecast data 912 and/or accessed and presented via the transfusion management application 408.

The supply demand monitoring component 904 can further evaluate the forecasted blood demand data in view of the current blood supply as provided by the blood bank systems 401 to regularly and/or continuously determine whether the demand exceeds the supply, and vice versa. In some embodiments, in the event of a blood shortage (e.g., the demand exceeds the supply) the alert component 906 can generate alerts 912 regarding imbalances in the supply and demand. These alerts can be provided to suitable entities (e.g., ordering clinicians, blood bank system administrators, etc.) via the transfusion management application 408 and/or via another notification system. The ordering component 908 can further automatically order the amount of blood needed to satisfy the demand.

In some embodiments, the ordering component 908 can also be configured to automatically order blood/blood products from one or more blood bank systems 901 for transfusion procedures determined to be appropriate by the transfusion appropriateness analysis component 108. For example, based on a determination that a transfusion procedure is appropriate for a patient and information identifying the recommended amount of blood product needed, the ordering component 908 can interface with the one or more blood bank systems 901 to identify a system that has an available supply of the blood product and order the blood product directly therefrom.

In some embodiments, the blood allocation component 910 can further schedule and coordinate allocating the distribution of blood resources from the blood bank systems 901 to satisfy the current and forecasted demand. In another embodiment, the supply/demand monitoring component 904 can predict waste volumes based on the tracked waste management data (e.g., determined by the waste management component 412). The ordering component 908 and/or the blood allocation component 910 can further facilitate reducing waste by adjusting ordered blood components centered on current clinical data of the patient population. This waste may be mitigated by considering alternative volumes and preparation times for specific patients, determining inventory requirements based on current and likely volumes so that the number of outdated or unused components can be reduced, and providing product components to the appropriate sites at the most ideal time.

Figure 10:
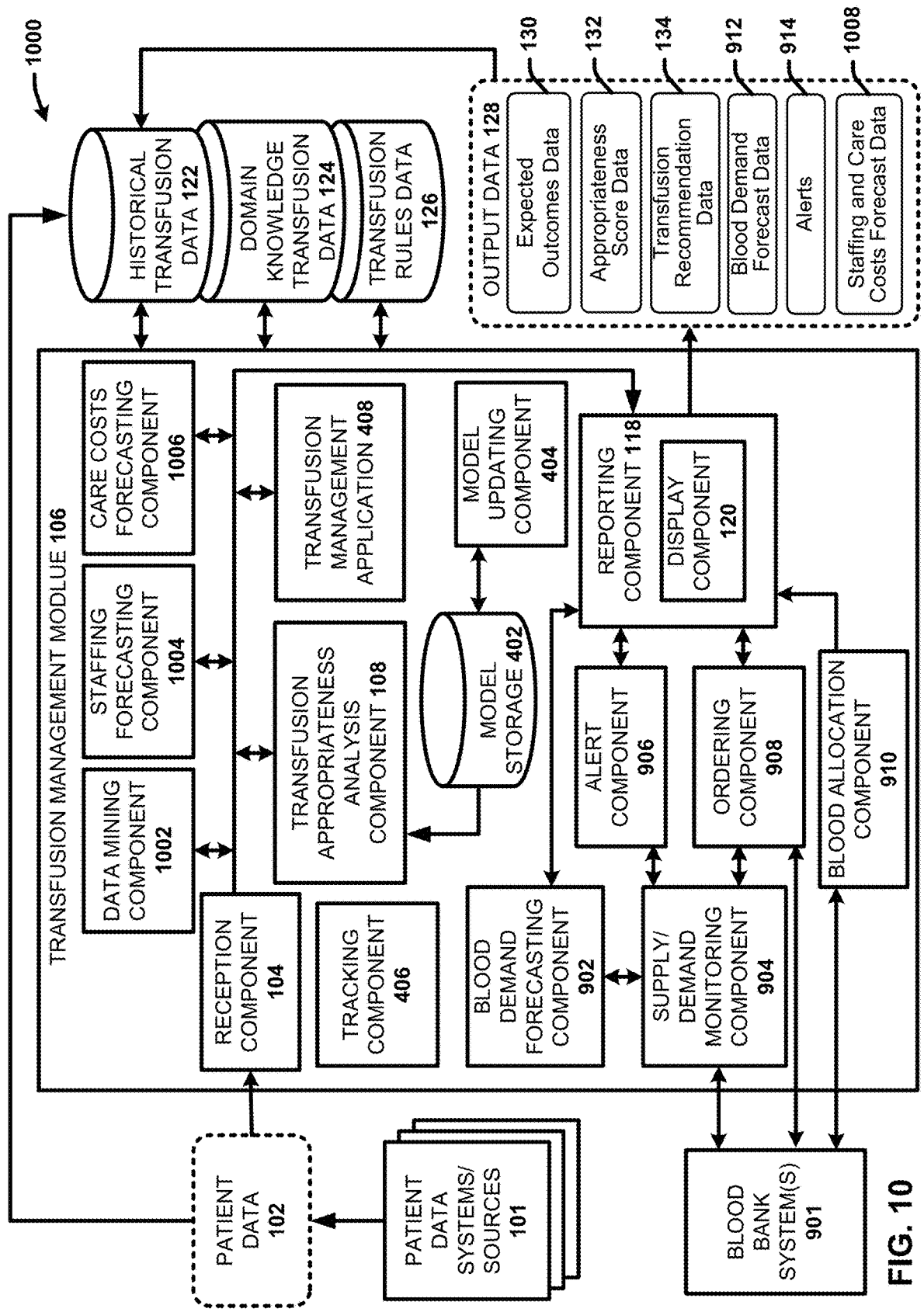
FIG. 10 illustrates a block diagram of another example, non-limiting system for managing blood transfusions using AI analytics in accordance with one or more embodiments of the disclosed subject matter.

FIG. 10 illustrates a block diagram of another example, non-limiting system 1000 for managing blood transfusions using AI analytics in accordance with one or more embodiments of the disclosed subject matter. System 1000 includes same or similar features and functionalities as system 900 with the addition of data mining component 1002, staffing forecasting component 1004 and care costs forecasting component 1006. Repetitive description of like elements employed in respective embodiments is omitted for sake of brevity.

In addition to extracting information for continual learning purposes and determining appropriateness of a blood transfusion for a patient, the transfusion management module 106 can also include data mining component 1002, staffing forecasting component 1004 and care costs forecasting component 1006. In one or more embodiments, the data mining component 1002 can perform the additional function of mining and correlating data from multiple data sources (e.g., EMR systems, blood bank systems 901, financial systems, surgical systems, etc.) for analytic purposes and to determine the risks and expected outcomes (expected outcomes data 130) of blood product transfusions for patients in the patient population. For instance, the financial data can be married to the clinical picture so that the business associated risks and outcomes can be determined. Data from multiple data sources may be used across the spectrum of care. For example, the data mining component 902 can also extract information regarding data products used, clinical responses, procedure details, and location of care. This additional data can also be used as input into the one or more TAAs to facilitate determining transfusion appropriateness to provide a more complete situational analysis.

For example, in some embodiments, the TAA can be configured employ this additional data to integrate a community risk and benefit analysis into a determination as to how appropriate a transfusion may be for a current patient at this current snapshot in time. Once these analytical predictions and outcomes have been determined, the results can be integrated with and visualized within the dashboard. This enables the provider to make intelligent decisions at the point of care. This is accomplished when system 1000 sends notification alerts to the provider at the time of ordering, where the essential purpose of the alert is to increase the provider's awareness of the patient's condition while simultaneously guiding the provider's decisions. System 1000 may also have the ability to review bypassed alerts as a point of quality assurance or performance improvement and can eliminate orders for components that will not likely be transfused.

In various embodiments, the transfusion appropriateness analysis component 108 can account for changes in the patient population. With these embodiments, the one or more TAAs can continually learn in an unsupervised manner and automatically adjust the transfusion appropriateness guidelines through the analysis of additional larger population data over time. The alert component 906 can notify providers regarding changes in relevant patient data and updated clinical guidelines. Therefore, the adjusted guidelines are incorporated into the system and contribute to the prediction of the risk, outcome, and complication probability.

In yet another embodiment, in addition to determining the appropriateness level of the transfusion and analyzing the results derived from a mining and correlating process (as described above), the transfusion management module 106 can forecast additional business management operations using the staffing forecasting component 904 and/or the care costs forecasting component 906. For example, the staffing forecasting component 904 can predict staffing (physicians, physician assistants, nurses, etc.) requirements based on the expected future transfusion rate and associated medical care for a location (floor, unit, etc.). This is especially useful in situations of highest efficiency when additional resources will be necessary to prepare components or transfuse them. In some implementations, the staffing forecasting component 904 can predict staffing at the blood banks (e.g., the blood bank systems 901) as well as determine future blood product utilization. The ordering component 908 can further automatically order blood products based on the expected need/demand and/or redistribute existing inventory based on the expected demand/need per blood bank location.

In another example, the transfusion management module 106 can predict future scheduled surgeries, current admissions, and the needs of chronic populations. In another embodiment, the care costs forecasting component 906 can predict the cost of care and potential cost savings based on the incremental direct and indirect costs of a transfusion procedure. The predicted cost of care can include the cost related to the length of stay, additional interventions, or transfusion complications. Once the predicted cost of care is determined for the patients in the patient population, the transfusion management module 106 can then compare specific patients in the larger community for greater understanding of how cost is impacted by interventions. The providers can then better implement best practices based on the resulting cost data. Information regarding forecasted staffing needs and care costs can further be included in the output data 128 (e.g., as staffing and care costs forecast data 1008).

Figure 11:
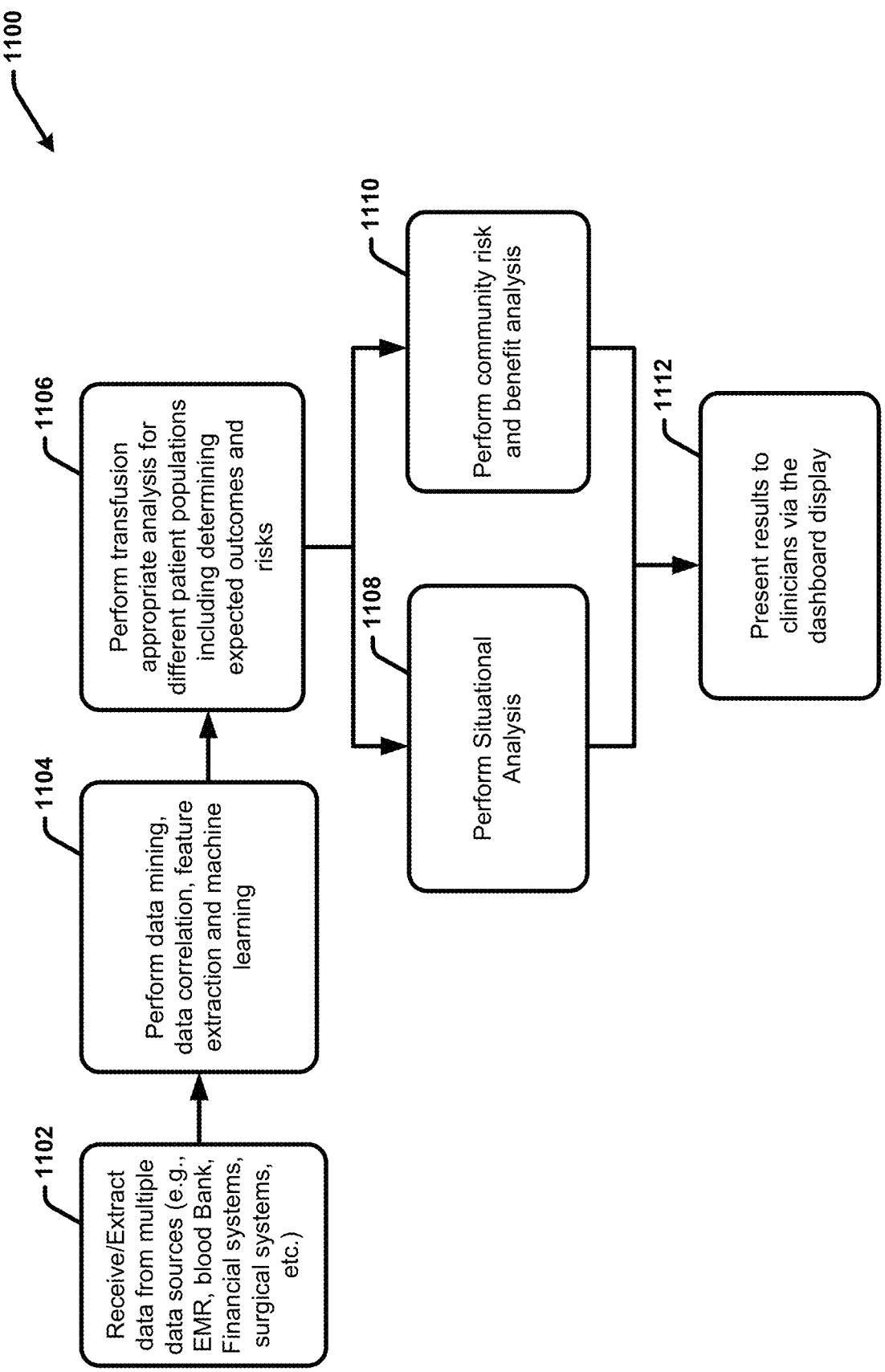
FIG. 11 presents a high-level flow diagram of another example computer implemented process for facilitating clinical decisions regarding blood transfusions in accordance with one or more embodiments of the disclosed subject matter.

FIG. 11 presents a high-level flow diagram of another example computer implemented process 1100 for facilitating clinical decisions regarding blood transfusions in accordance with one or more embodiments of the disclosed subject matter. Repetitive description of like elements employed in respective embodiments is omitted for sake of brevity.

As shown in FIG. 11, at 1102, a system operatively coupled to a processor (e.g., system 100, system 400, system 900, system 100 and the like), can receive/extract data from multiple data sources (e.g., patient data sources/systems 101, EMR systems, blood bank systems 901, financial systems, surgical systems, etc.). At 1104, the system can perform data mining, data correlation, feature extraction and machine learning. At 1106, the system can perform transfusion appropriate analysis for different patient populations or patient groups, including determining expected outcomes and risks. At 1108, the system can perform situational analysis. At 1110, the system can perform community risk and benefit analysis. At 1112, the system can present the results to clinicians via a dashboard display of the transfusion management application 408.

Figure 12:
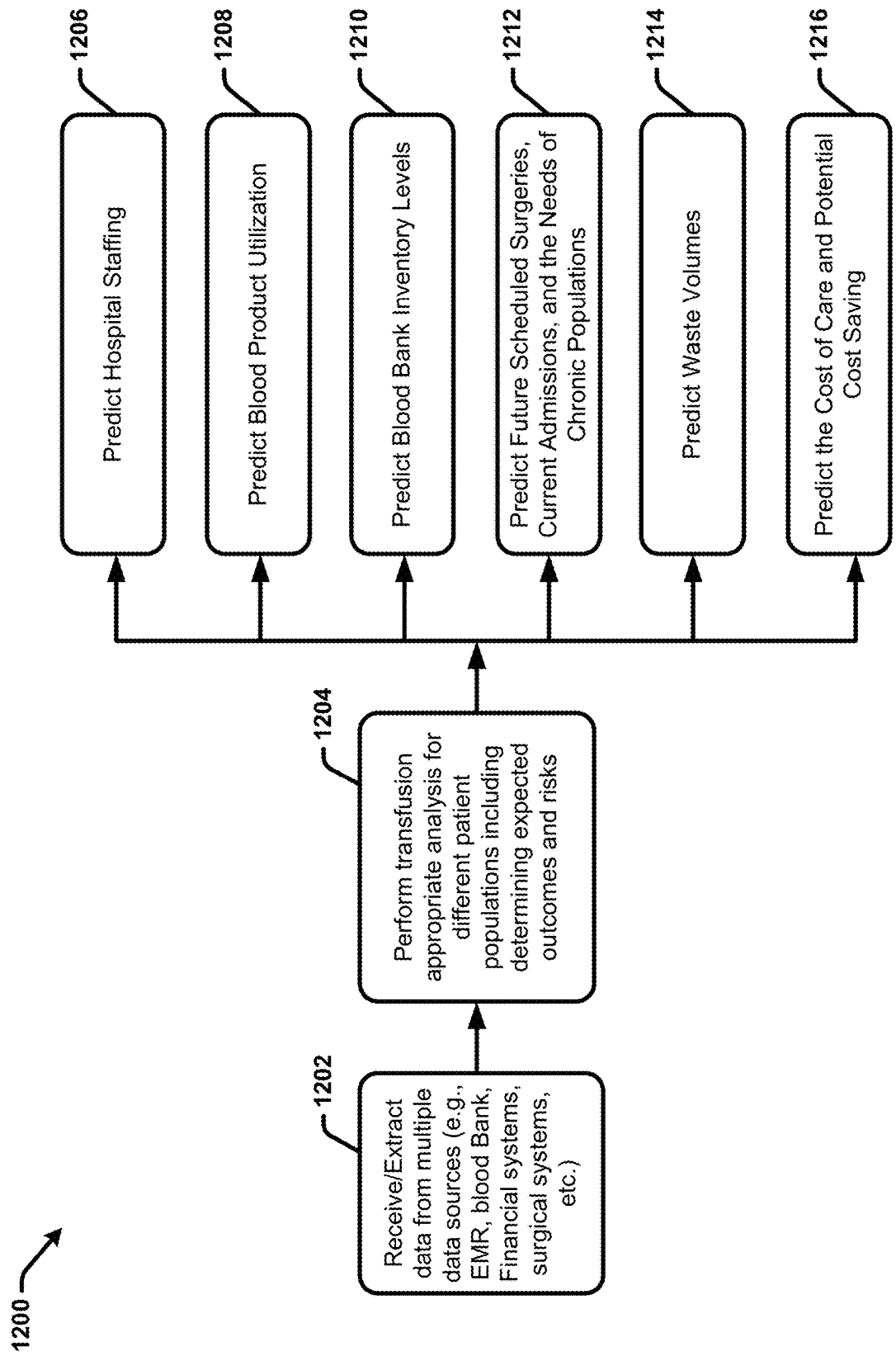
FIG. 12 presents a high-level flow diagram of an example computer implemented process forecasting resource utilization, staffing information, costs of care, and additional hospital management information based in part on predicted blood transfusion demand in accordance with one or more embodiments of the disclosed subject matter.

FIG. 12 presents a high-level flow diagram of an example computer implemented process 1200 forecasting resource utilization, staffing information, costs of care, and additional hospital management information based in part on predicted blood transfusion demand in accordance with one or more embodiments of the disclosed subject matter. Repetitive description of like elements employed in respective embodiments is omitted for sake of brevity.

As shown in FIG. 12, at 1202, a system operatively coupled to a processor (e.g., system 100, system 400, system 900, system 1000 and the like), can receive/extract data from multiple data sources (e.g., patient data sources/systems 101, EMR systems, blood bank systems 901, financial systems, surgical systems, etc.). At 1204, the system can perform transfusion appropriate analysis for different patient populations or patient groups including determining expected outcomes and risks. At 1206, the system can predict hospital staffing information. At 1208, the system can predict blood product utilization information. At 1210 the system can predict blood ban inventory levels. At 1212, the system can predict future scheduled surgeries, current admission and the needs of chronic populations. At 1214 the system can predict waste volumes, and at 1216, the system can predict cost of care and potential cost savings that could be realized based on minimizing the predicted waste volumes.

Figure 13:
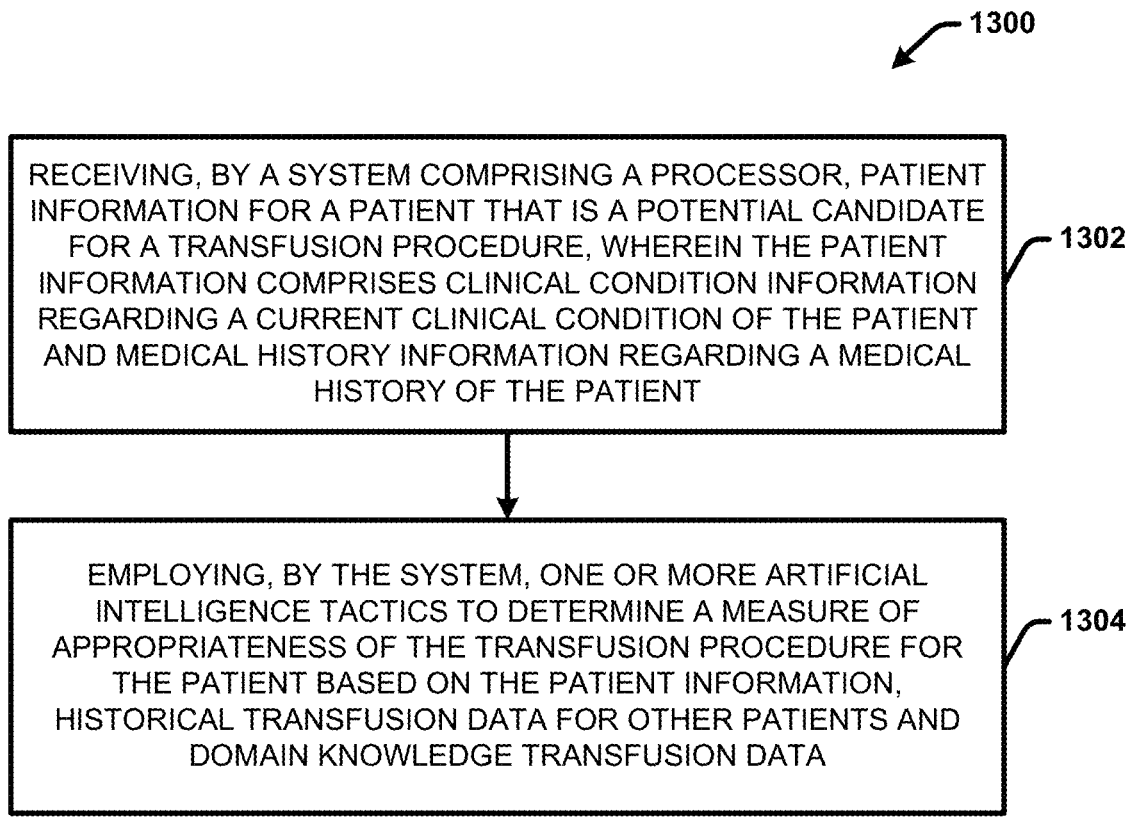
FIG. 13 presents a high-level flow diagram of another example computer implemented process for facilitating clinical decisions regarding blood transfusions in accordance with one or more embodiments of the disclosed subject matter.

FIG. 13 presents a high-level flow diagram of another example computer implemented process 1300 for facilitating clinical decisions regarding blood transfusions in accordance with one or more embodiments of the disclosed subject matter.

In accordance with method 1300, at 1302, a system comprising a processor (e.g., system 100, system 400, system 900 or system 1000), receives (e.g., via reception component 104) patient information (e.g., patient data 102) for a patient that is a potential candidate for a transfusion procedure, wherein the patient information comprises clinical condition information regarding a current clinical condition of the patient and medical history information regarding a medical history of the patient. At 1304, the system employs one or more artificial intelligence tactics to determine a measure of appropriateness (e.g., appropriateness score data 132) of the transfusion procedure for the patient based on the patient information, historical transfusion data for other patients and domain knowledge transfusion data (e.g., via the transfusion appropriateness analysis component 108).

Figure 14:
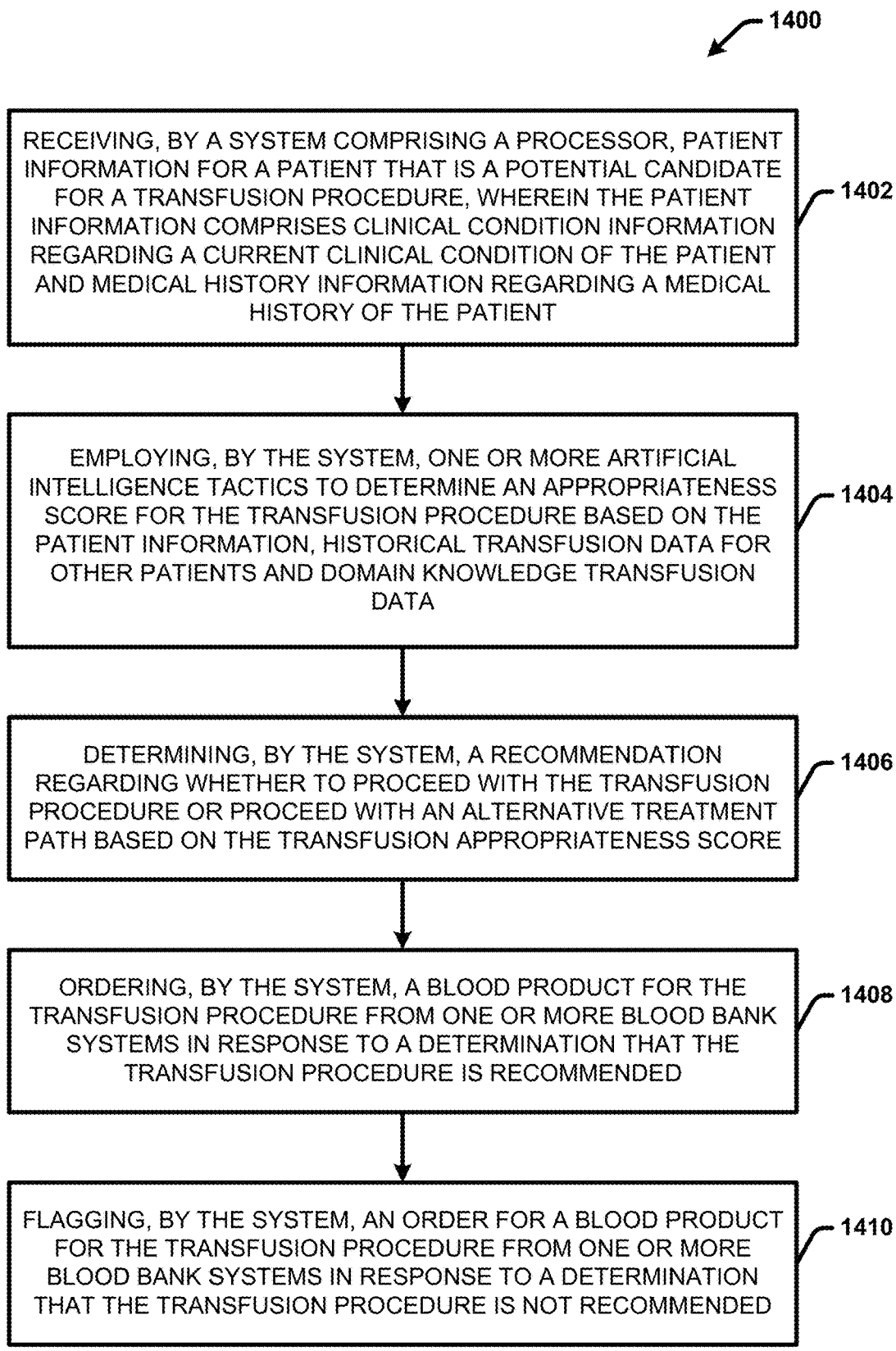
FIG. 14 presents a high-level flow diagram of another example computer implemented process for facilitating clinical decisions regarding blood transfusions in accordance with one or more embodiments of the disclosed subject matter.

FIG. 14 presents a high-level flow diagram of another example computer implemented process 1400 for facilitating clinical decisions regarding blood transfusions in accordance with one or more embodiments of the disclosed subject matter.

In accordance with method 1400, at 1402, a system comprising a processor (e.g., system 100, system 400, system 900 or system 1000), receives (e.g., via reception component 104) patient information (e.g., patient data 102) for a patient that is a potential candidate for a transfusion procedure, wherein the patient information comprises clinical condition information regarding a current clinical condition of the patient and medical history information regarding a medical history of the patient. At 1404, the system employs one or more artificial intelligence tactics to determine an appropriateness score (e.g., appropriateness score data 132) for the transfusion procedure for the patient based on the patient information, historical transfusion data for other patients and domain knowledge transfusion data (e.g., via the transfusion appropriateness analysis component 108). At 1406, the system determines a recommendation (e.g., transfusion recommendation data 134) regarding whether to proceed with the transfusion procedure or proceed with an alternative treatment path based on the transfusion appropriateness score (e.g., using transfusion recommendation component 116). At 1408, the system orders a blood product for the transfusion procedure from one or more blood bank systems in response to a determination that the transfusion procedure is recommended (e.g., using ordering component 908). At 1410, the system flags an order for a blood product for the transfusion procedure from one or more blood bank systems in response to a determination that the transfusion procedure is not recommended (e.g., using the waste management component 412).

Figure 15:
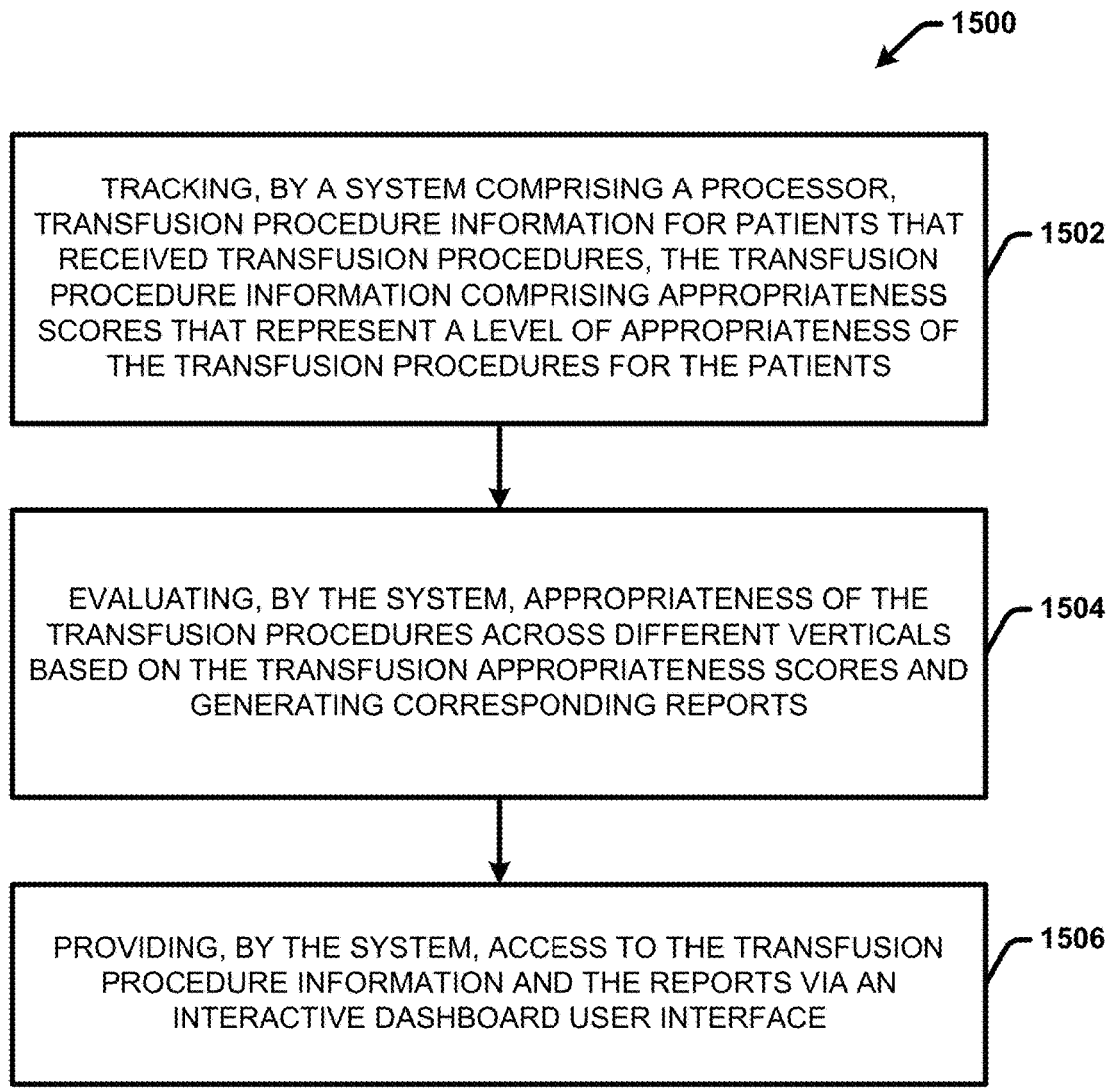
FIG. 15 presents a high-level flow diagram of another example computer implemented process for facilitating clinical decisions regarding blood transfusions in accordance with one or more embodiments of the disclosed subject matter.

FIG. 15 presents a high-level flow diagram of another example computer implemented process 1500 for facilitating clinical decisions regarding blood transfusions in accordance with one or more embodiments of the disclosed subject matter.

In accordance with method 1500, at 1502, a system comprising a processor (e.g., system 100, system 400, system 900 or system 1000), tracks procedure information for patients that received transfusion procedures (e.g., using tracking component 406), the transfusion procedure information comprising appropriateness scores that represent a level of appropriateness of the transfusion procedures for the patients. At 1504, the system evaluates appropriateness of the transfusion procedures across different verticals based on the transfusion appropriateness scores and generates corresponding reports (e.g., via the performance evaluation component 410). At 1506, the system provides access to the transfusion procedure information and the reports via an interactive dashboard user interface (e.g., via the transfusion management application 408).

Figure 16:
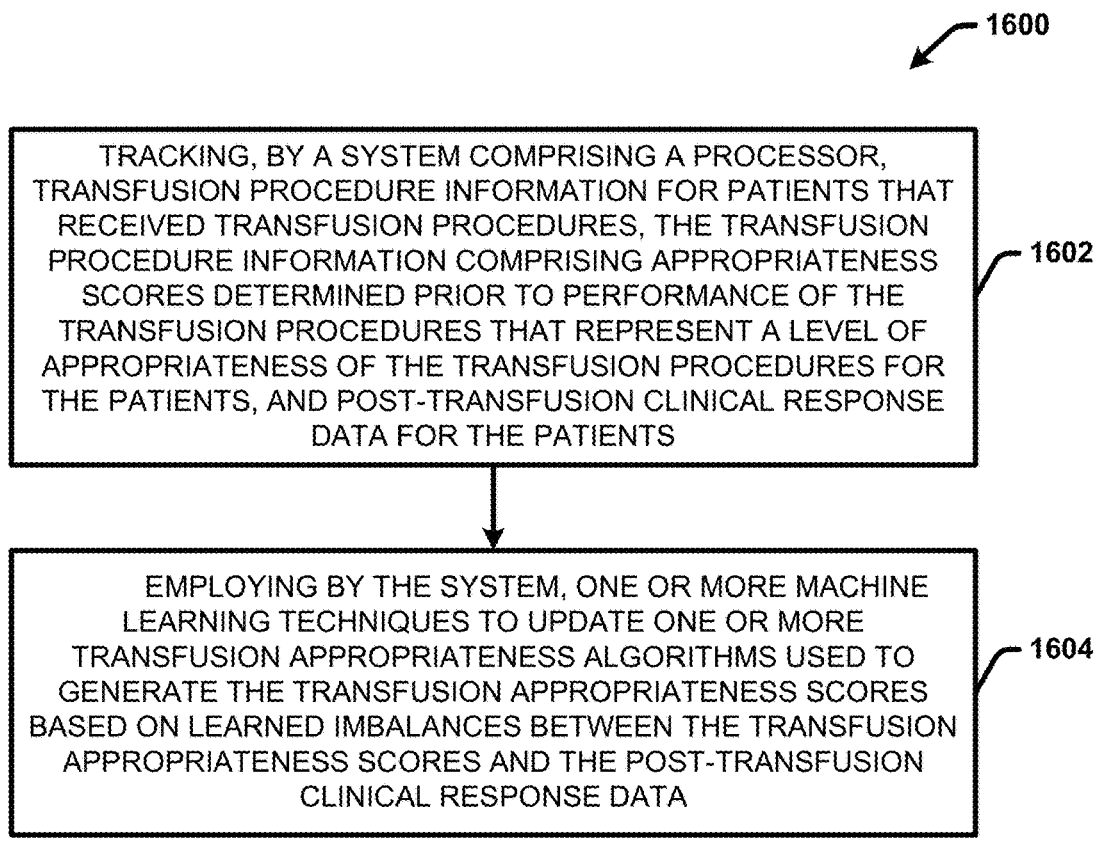
FIG. 16 presents a high-level flow diagram of another example computer implemented process for facilitating clinical decisions regarding blood transfusions in accordance with one or more embodiments of the disclosed subject matter.

FIG. 16 presents a high-level flow diagram of another example computer implemented process 1600 for facilitating clinical decisions regarding blood transfusions in accordance with one or more embodiments of the disclosed subject matter.

In accordance with method 1600, at 1602, a system comprising a processor (e.g., system 100, system 400, system 900 or system 1000), tracks procedure information for patients that received transfusion procedures (e.g., using tracking component 406), the transfusion procedure information comprising appropriateness scores determined prior to performance of the transfusion procedures that represent a level of appropriateness of the transfusion procedures for the patients, and post-transfusion clinical response data for the patients. At 1604, the system employs one or more machine learning techniques to update one or more transfusion appropriateness algorithms used to generate the transfusion appropriateness scores based on learned clinical imbalances between the transfusion appropriateness scores and the post-transfusion clinical response data.

It should be noted that, for simplicity of explanation, in some circumstances the computer-implemented methodologies are depicted and described herein as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 17:
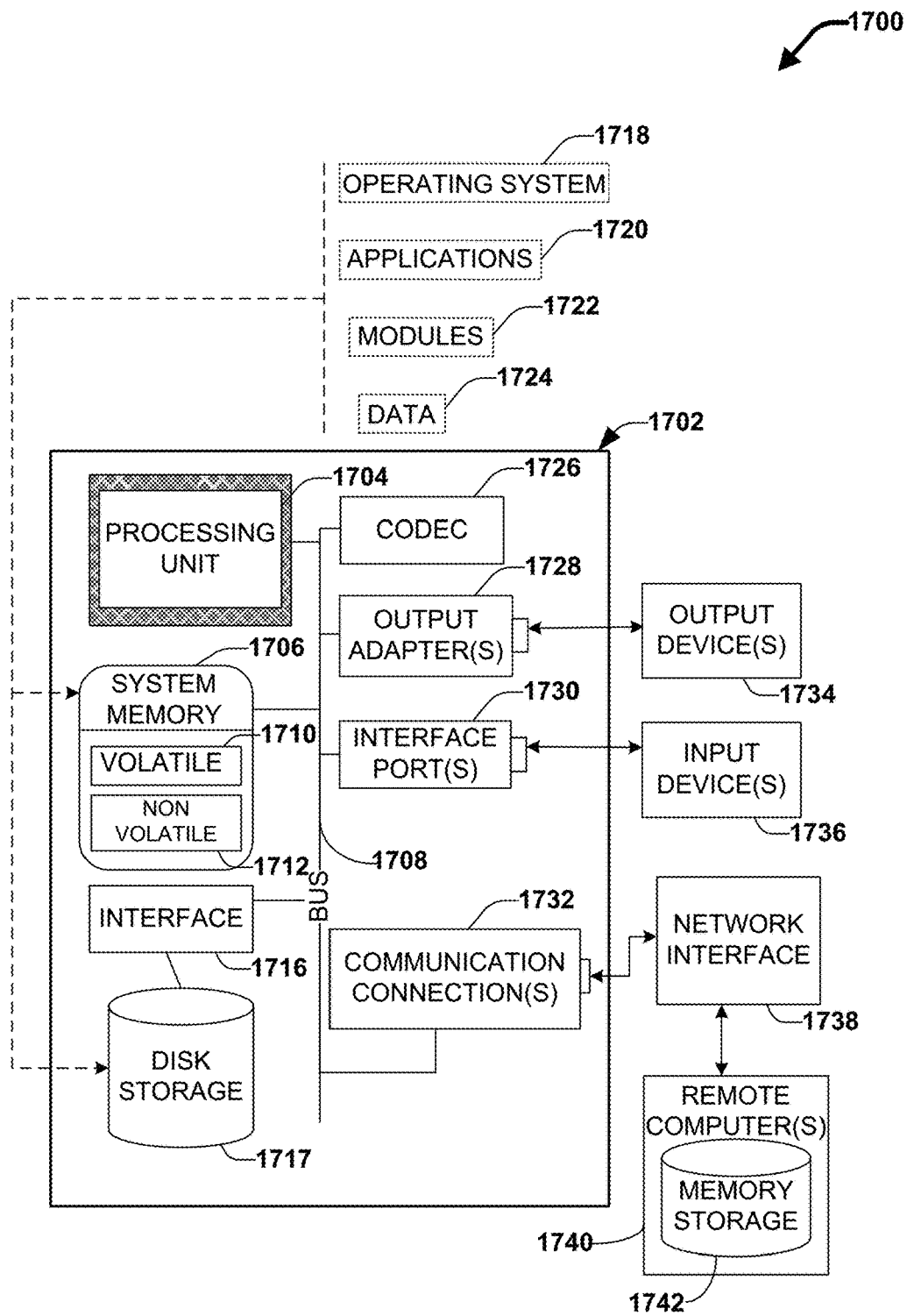
FIG. 17 illustrates a block diagram of an example, non-limiting operating environment in which one or more embodiments described herein can be facilitated.

FIG. 17 can provide a non-limiting context for the various aspects of the disclosed subject matter, intended to provide a general description of a suitable environment in which the various aspects of the disclosed subject matter can be implemented. FIG. 17 illustrates a block diagram of an example, non-limiting operating environment in which one or more embodiments described herein can be facilitated. Repetitive description of like elements employed in other embodiments described herein is omitted for sake of brevity.

With reference to FIG. 17, a suitable operating environment 1700 for implementing various aspects of this disclosure can also include a computer 1702. The computer 1702 can also include a processing unit 1704, a system memory 1706, and a system bus 1708. The system bus 1708 couples system components including, but not limited to, the system memory 1706 to the processing unit 1704. The processing unit 1704 can be any of various available processors. Dual microprocessors and other multiprocessor architectures also can be employed as the processing unit 1704. The system bus 1708 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MCA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 17124), and Small Computer Systems Interface (SCSI).

The system memory 1706 can also include volatile memory 1710 and nonvolatile memory 1712. The basic input/output system (BIOS), containing the basic routines to transfer information between elements within the computer 1702, such as during start-up, is stored in nonvolatile memory 1712. Computer 1702 can also include removable/non-removable, volatile/non-volatile computer storage media. FIG. 17 illustrates, for example, a disk storage 1714. Disk storage 1714 can also include, but is not limited to, devices like a magnetic disk drive, floppy disk drive, tape drive, Jaz drive, Zip drive, LS-100 drive, flash memory card, or memory stick. The disk storage 1714 also can include storage media separately or in combination with other storage media. To facilitate connection of the disk storage 1714 to the system bus 1708, a removable or non-removable interface is typically used, such as interface 1716. FIG. 17 also depicts software that acts as an intermediary between users and the basic computer resources described in the suitable operating environment 1700. Such software can also include, for example, an operating system 1718. Operating system 1718, which can be stored on disk storage 1714, acts to control and allocate resources of the computer 1702.

System applications 1720 take advantage of the management of resources by operating system 1718 through program modules 1722 and program data 1724, e.g., stored either in system memory 1706 or on disk storage 1714. It is to be appreciated that this disclosure can be implemented with various operating systems or combinations of operating systems. A user enters commands or information into the computer 1702 through input device(s) 1736. Input devices 1736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1704 through the system bus 1708 via interface port(s) 1730. Interface port(s) 1730 include, for example, a serial port, a parallel port, a game port, and a universal serial bus (USB). Output device(s) 1734 use some of the same type of ports as input device(s) 1736. Thus, for example, a USB port can be used to provide input to computer 1702, and to output information from computer 1702 to an output device 1734. Output adapter 1728 is provided to illustrate that there are some output devices 1734 like monitors, speakers, and printers, among other output devices 1734, which require special adapters. The output adapters 1728 include, by way of illustration and not limitation, video and sound cards that provide a means of connection between the output device 1734 and the system bus 1708. It should be noted that other devices and/or systems of devices provide both input and output capabilities such as remote computer(s) 1740.

Computer 1702 can operate in a networked environment using logical connections to one or more remote computers, such as remote computer(s) 1740. The remote computer(s) 1740 can be a computer, a server, a router, a network PC, a workstation, a microprocessor based appliance, a peer device or other common network node and the like, and typically can also include many or all of the elements described relative to computer 1702. For purposes of brevity, only a memory storage device 1742 is illustrated with remote computer(s) 1740. Remote computer(s) 1740 is logically connected to computer 1702 through a network interface 1738 and then physically connected via communication connection 1732. Network interface 1738 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1732 refers to the hardware/software employed to connect the network interface 1738 to the system bus 1708. While communication connection 1732 is shown for illustrative clarity inside computer 1702, it can also be external to computer 1702. The hardware/software for connection to the network interface 1738 can also include, for exemplary purposes only, internal and external technologies such as, modems including regular telephone grade modems, cable modems and DSL modems, ISDN adapters, and Ethernet cards.

One or more embodiments described herein can be a system, a method, an apparatus and/or a computer program product at any possible technical detail level of integration. The computer program product can include a computer readable storage medium (or media) having computer readable program instructions thereon for causing a processor to carry out aspects of one or more embodiment. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. In this regard, in various embodiments, a computer readable storage medium as used herein can include non-transitory and tangible computer readable storage mediums.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of one or more embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of one or more embodiments.

Aspects of one or more embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and other devices to function in a particular manner, such that the computer readable storage medium having instructions stored therein comprises an article of manufacture including instructions which implement aspects of the function/act specified in the flowchart and block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and block diagram block or blocks.

The flowchart and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and flowchart illustration, and combinations of blocks in the block diagrams and flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on one or more computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and a computer. By way of illustration, both an application running on a server and the server can be a component. One or more components can reside within a process or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that can provide specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

The term "facilitate" as used herein is in the context of a system, device or component "facilitating" one or more actions or operations, in respect of the nature of complex computing environments in which multiple components and/or multiple devices can be involved in some computing operations. Non-limiting examples of actions that may or may not involve multiple components and/or multiple devices comprise transmitting or receiving data, establishing a connection between devices, determining intermediate results toward obtaining a result (e.g., including employing ML and/or AI techniques to determine the intermediate results), etc. In this regard, a computing device or component can facilitate an operation by playing any part in accomplishing the operation. When operations of a component are described herein, it is thus to be understood that where the operations are described as facilitated by the component, the operations can be optionally completed with the cooperation of one or more other computing devices or components, such as, but not limited to: sensors, antennae, audio and/or visual output devices, other devices, etc.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches, and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components;
   a processor that executes computer executable components stored in the memory, wherein the computer executable components comprise:
   a reception component that receives patient information for a patient that is a potential candidate for a transfusion procedure, wherein the patient information comprises clinical condition information regarding a current clinical condition of the patient, and medical history information regarding a medical history of the patient;
   an outcomes forecasting component that employs one or more first machine learning processes to forecast expected outcomes of the transfusion procedure based on the patient information, historical transfusion data for other patients associated with a similar clinical context of the patient, and domain knowledge transfusion, wherein the expected outcomes include potential adverse outcomes and likelihood of occurrence of the adverse outcomes, and wherein the one or more first machine learning processes comprise:
      generating a feature vector representation for the patient information using a dimensionality reduction model;
      identifying the subset of similar patients to the patient included in the historical transfusion data based on matching the feature vector representation with reference feature vectors generated for the similar patients using the dimensionality reduction model, and
      evaluating historical outcomes for the similar patients; and
   a transfusion appropriateness analysis component that employs one or more second machine learning processes to determine a measure of appropriateness of the transfusion procedure for the patient based on the expected outcomes, the patient information, the historical transfusion data for the other patients and the domain knowledge transfusion data.

2. The system of claim 1, wherein the measure of appropriateness comprises a transfusion appropriateness score, and wherein the computer executable components further comprise:
   a recommendation component that determines a recommendation regarding whether to proceed with the transfusion procedure or proceed with an alternative treatment path based on the transfusion appropriateness score and a threshold score.

3. The system of claim 2, wherein the computer executable components further comprise:
   an ordering component that interfaces with one or more blood bank systems and orders a blood product for the transfusion procedure in response to a determination that the transfusion procedure is recommended.

4. The system of claim 1, wherein the one or more second machine learning processes comprise employing a transfusion appropriateness algorithm that generates the measure of appropriateness based on a plurality of input variables included in the patient information and the expected outcomes.

5. The system of claim 4, wherein the transfusion appropriateness algorithm comprises one or more machine learning algorithms that learn correlations between the plurality of input variables and appropriateness levels of transfusion procedures based on analysis of the historical transfusion data and the domain knowledge transfusion data, wherein the one or more machine learning algorithms learn the correlations based on clustering of patients into different patient groups, and wherein the levels of appropriates are tailored to the different patient groups.

6. The system of claim 1, wherein the one or more second machine learning processes comprise determining the measure of appropriateness based on outcomes of transfusion procedures performed for the subset of similar patients.

7. The system of claim 2, wherein the computer executable components further comprise:
   an amount forecasting component that forecasts, in response to a determination that the transfusion procedure is recommended, an amount of blood product for the transfusion procedure based on the patient data, the measure of appropriateness, the historical transfusion data for other patients and the domain knowledge transfusion data.

8. The system of claim 1, wherein the dimensionality reduction model comprises an autoencoder trained on the historical transfusion data for the other patients.

9. The system of claim 2, wherein the computer executable components comprise:
   a waste management component that:
      identifies a medical provider that consistently performs transfusion procedures against recommendations generated by the transfusion appropriateness analysis component based on the transfusion procedures receiving transfusion appropriateness scores below the threshold score, and
      monitors new recommendations generated by the transfusion appropriateness analysis component for new patients associated with the medical care provider based on the identification.

10. The system of claim 9, wherein the waste management component notifies an administrator based on a new patient of the new patients receiving a transfusion appropriateness score below the threshold score, thereby deterring performance of inappropriate transfusion procedures by the administrator.

11. The system of claim 9, wherein the waste management component prevents orders for blood products from the medical care provider without additional authorization based on the identification, thereby minimizing waste of blood product resources.

12. A computer-implemented method, comprising:
    receiving, by a system comprising a processor, patient information for a patient that is a potential candidate for a transfusion procedure, wherein the patient information comprises clinical condition information regarding a current clinical condition of the patient and medical history information regarding a medical history of the patient;
    employing, by the system, one or more first machine learning processes to forecast expected outcomes of the transfusion procedure based on the patient information, historical transfusion data for other patients associated with a similar clinical context of the patient, and domain knowledge transfusion, wherein the expected outcomes include potential adverse outcomes and likelihood of occurrence of the adverse outcomes, and wherein employing the one or more first machine learning processes comprises:
  generating a feature vector representation for the patient information using a dimensionality reduction model;
  identifying the subset of similar patients to the patient included in the historical transfusion data based on matching the feature vector representation with reference feature vectors generated for the similar patients using the dimensionality reduction model, and
  evaluating historical outcomes for the similar patients; and
employing, by the system, one or more second machine learning processes to determine a measure of appropriateness of the transfusion procedure for the patient based on the expected outcomes, the patient information, the historical transfusion data for the other patients and the domain knowledge transfusion data.

13. The method of claim 12, wherein the measure of appropriateness comprises a transfusion appropriateness score, and wherein the method further comprises:
  determining, by the system, a recommendation regarding whether to proceed with the transfusion procedure or proceed with an alternative treatment path based on the transfusion appropriateness score; and
  presenting, by the system, recommendation data describing the recommendation to a clinician to facilitate clinical decision making for the patient prior to performance of the transfusion procedure.

14. The method of claim 13, further comprising:
  ordering, by the system, a blood product for the transfusion procedure from one or more blood bank systems in response to a determination that the transfusion procedure is recommended.

15. The method of claim 13, further comprising:
  identifying, by the system, an order for a blood product for the transfusion procedure from one or more blood bank systems in response to a determination that the transfusion procedure is not recommended; and
  preventing, by the system, the order from being fulfilled based on the identifying.

16. The method of claim 12, wherein the one or more second machine learning processes comprise employing a transfusion appropriateness algorithm to generate the measure of appropriateness based on a plurality of input variables included in the patient information, and wherein the transfusion appropriateness algorithm comprises one or more machine learning algorithms that learn correlations between the plurality of input variables and appropriateness levels of transfusion procedures based on analysis of the historical transfusion data and the domain knowledge transfusion data.

17. A non-transitory machine-readable storage medium, comprising executable instructions that, when executed by a processor of a device, facilitate performance of operations, comprising:
  receiving patient information for a patient that is a potential candidate for a transfusion procedure, wherein the patient information comprises condition information regarding a current medical condition of the patient and medical history information regarding a medical history of the patient;
  employing one or more first machine learning processes to forecast expected outcomes of the transfusion procedure based on the patient information, historical transfusion data for other patients associated with a similar clinical context of the patient, and domain knowledge transfusion, wherein the expected outcomes include potential adverse outcomes and likelihood of occurrence of the adverse outcomes, and wherein employing the one or more first machine learning processes comprises:
    generating a feature vector representation for the patient information using a dimensionality reduction model;
    identifying the subset of similar patients to the patient included in the historical transfusion data based on matching the feature vector representation with reference feature vectors generated for the similar patients using the dimensionality reduction model, and
    evaluating historical outcomes for the similar patients; and
  employing one or more second machine learning processes to determine a measure of appropriateness of the transfusion procedure for the patient based on the expected outcomes, the patient information, the historical transfusion data for the other patients and the domain knowledge transfusion data.

18. The non-transitory machine-readable storage medium of claim 17, wherein the measure of appropriateness comprises a transfusion appropriateness score, and wherein the operations further comprise:
  determining a recommendation regarding whether to proceed with the transfusion procedure or proceed with an alternative treatment path based on the transfusion appropriateness score; and
  presenting recommendation data describing the recommendation to a clinician to facilitate clinical decision making for the patient prior to performance of the transfusion procedure.

19. The non-transitory machine-readable storage medium of claim 17, wherein the dimensionality reduction model comprises an autoencoder trained on the historical transfusion data for the other patients.

20. The non-transitory machine-readable storage medium of claim 17, wherein the one or more second machine learning processes comprise determining the measure of appropriateness based on outcomes of transfusion procedures performed for the subset of similar patients.

* * * * *